United States Patent
Grady et al.

(10) Patent No.: US 8,628,643 B2
(45) Date of Patent: *Jan. 14, 2014

(54) PROCESS TO REMOVE PRODUCT ALCOHOL FROM A FERMENTATION BY VAPORIZATION UNDER VACUUM

(75) Inventors: Michael Charles Grady, Oaklyn, NJ (US); William D. Parten, Wilmington, DE (US); Robert W. Sylvester, Newark, DE (US); Joseph J. Zaher, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/207,388

(22) Filed: Aug. 10, 2011

(65) Prior Publication Data

US 2012/0211348 A1 Aug. 23, 2012

Related U.S. Application Data

(60) Provisional application No. 61/379,546, filed on Sep. 2, 2010, provisional application No. 61/427,896, filed on Dec. 29, 2010, provisional application No. 61/440,034, filed on Feb. 7, 2011.

(51) Int. Cl.
| | | |
|---|---|---|
| *B01D 3/10* | (2006.01) | |
| *B01D 53/14* | (2006.01) | |
| *B01D 53/62* | (2006.01) | |
| *C07C 31/12* | (2006.01) | |
| *B01D 3/14* | (2006.01) | |
| *B01D 3/34* | (2006.01) | |

(52) U.S. Cl.
USPC ........... 203/42; 95/158; 95/183; 95/209; 95/230; 203/2; 203/39; 203/81; 203/84; 203/DIG. 8; 435/157; 435/160; 568/917

(58) Field of Classification Search
USPC ............ 203/2, 14, 39, 42, 49, 81, 84, DIG. 8; 568/916, 917; 95/149, 158, 183, 209, 95/230, 231, 236; 435/157, 160
See application file for complete search history.

(56) References Cited

U.S. PATENT DOCUMENTS

| | | | |
|---|---|---|---|
| 3,261,766 A | * | 7/1966 | Sherwood ..................... 203/11 |
| 4,101,297 A | | 7/1978 | Uda et al. |

(Continued)

FOREIGN PATENT DOCUMENTS

| | | |
|---|---|---|
| EP | 0173544 | 5/1991 |
| FR | 2933008 | 1/2010 |

(Continued)

OTHER PUBLICATIONS

International Search Report and Written Opinion of corresponding PCT/US2011/024159 mailed Oct. 28, 2011.

(Continued)

*Primary Examiner* — Virginia Manoharan
(74) *Attorney, Agent, or Firm* — Christine M. Lhulier

(57) ABSTRACT

A fermentation liquid feed including water and a product alcohol and optionally $CO_2$ is at least partially vaporized such that a vapor stream is produced. The vapor stream is contacted with an absorption liquid under suitable conditions wherein an amount of the product alcohol is absorbed. The portion of the vapor stream that is absorbed can include an amount of each of the water, the product alcohol and optionally the $CO_2$. The temperature at the onset of the absorption of the vapor stream into the absorption liquid can be greater than the temperature at the onset of condensation of the vapor stream in the absence of the absorption liquid. The product alcohol can be separated from the absorption liquid whereby the absorption liquid is regenerated. The absorption liquid can include a water soluble organic molecule such as an amine.

18 Claims, 20 Drawing Sheets

(56) References Cited

U.S. PATENT DOCUMENTS

| | | | | |
|---|---|---|---|---|
| 4,169,010 | A * | 9/1979 | Marwil | 435/247 |
| 4,209,364 | A * | 6/1980 | Rothschild | 203/11 |
| 4,303,478 | A | 12/1981 | Field et al. | |
| 4,349,628 | A | 9/1982 | English et al. | |
| 4,359,533 | A | 11/1982 | Wilke et al. | |
| 4,366,032 | A | 12/1982 | Mikitenko et al. | |
| 4,399,000 | A | 8/1983 | Tedder | |
| 4,538,010 | A | 8/1985 | Diana | |
| 4,708,775 | A | 11/1987 | McGregor et al. | |
| 4,846,240 | A * | 7/1989 | Erickson | 159/24.2 |
| 4,996,038 | A * | 2/1991 | McAlister et al. | 423/522 |
| 5,084,142 | A | 1/1992 | Berg et al. | |
| 5,271,914 | A | 12/1993 | Sugimoto et al. | |
| 5,961,789 | A | 10/1999 | Berg | |
| 5,993,608 | A | 11/1999 | Abry et al. | |
| 6,117,275 | A | 9/2000 | Baumann | |
| 6,136,577 | A | 10/2000 | Gaddy | |
| 6,284,023 | B1 | 9/2001 | Torkildsen et al. | |
| 6,306,307 | B1 | 10/2001 | McGregor et al. | |
| 6,461,413 | B1 | 10/2002 | Landreau et al. | |
| 7,074,258 | B2 | 7/2006 | Collins et al. | |
| 7,419,646 | B2 | 9/2008 | Cadours et al. | |
| 7,531,688 | B2 | 5/2009 | Fleisher | |
| 7,566,383 | B2 | 7/2009 | Everett et al. | |
| 7,601,377 | B2 | 10/2009 | Aksenov et al. | |
| 7,666,282 | B2 | 2/2010 | Sylvester et al. | |
| 7,759,393 | B2 | 7/2010 | Joerger et al. | |
| 8,101,808 | B2 * | 1/2012 | Evanko et al. | 568/916 |
| 2002/0072100 | A1 | 6/2002 | Lightner | |
| 2003/0143704 | A1 | 7/2003 | Lightner | |
| 2006/0156923 | A1 | 7/2006 | Meckl et al. | |
| 2007/0031918 | A1 | 2/2007 | Dunson, Jr. et al. | |
| 2007/0092957 | A1 | 4/2007 | Donaldson et al. | |
| 2007/0148069 | A1 | 6/2007 | Chakravarti et al. | |
| 2007/0259410 | A1 | 11/2007 | Donaldson et al. | |
| 2008/0182308 | A1 | 7/2008 | Donaldson et al. | |
| 2009/0283398 | A1 | 11/2009 | Noro et al. | |
| 2009/0293723 | A1 | 12/2009 | Steele | |
| 2009/0305363 | A1 | 12/2009 | Anthony et al. | |
| 2009/0305370 | A1 | 12/2009 | Grady et al. | |
| 2010/0011958 | A1 | 1/2010 | Cadours et al. | |
| 2010/0062926 | A1 | 3/2010 | Woodhouse et al. | |
| 2010/0104490 | A1 | 4/2010 | Bouillon et al. | |
| 2010/0143993 | A1 | 6/2010 | Erdner-Tindall et al. | |
| 2010/0143994 | A1 | 6/2010 | Erdner-Tindall et al. | |
| 2010/0143995 | A1 | 6/2010 | Erdner-Tindall et al. | |
| 2010/0240524 | A1 * | 9/2010 | Hilaly et al. | 502/34 |
| 2011/0088553 | A1 | 4/2011 | Woodhouse et al. | |
| 2011/0117633 | A1 | 5/2011 | McGregor et al. | |
| 2011/0124060 | A1 | 5/2011 | Anthony et al. | |
| 2011/0168019 | A1 | 7/2011 | Northrop et al. | |
| 2012/0156738 | A1 | 6/2012 | Anton et al. | |

FOREIGN PATENT DOCUMENTS

| | | |
|---|---|---|
| WO | 2007075399 | 7/2007 |
| WO | 2008021700 | 2/2008 |
| WO | 2009079362 | 6/2009 |
| WO | 2009108503 | 9/2009 |
| WO | 2010024714 | 3/2010 |
| WO | 2010121374 | 10/2010 |
| WO | 2010151832 | 12/2010 |
| WO | 2011003962 | 1/2011 |

OTHER PUBLICATIONS

Roffler, Extractive fermentation—lactic acid and acetone/butanol production, Doctoral Dissertation, 1986, Department of Chemical Engineering at the University of California at Berkeley.

Olah et al., Chemical Recycling of Carbon Dioxide to Methanol and Dimethyl Ether: From Greenhouse Gas to Renewable, Environmentally Carbon Neutral Fuels and Synthetic Hydrocarbons, Journal of Organic Chemistry, 2009, 487-498, 74, 2, American Chemical Society, United States.

Shi, et al., Performance Evaluation of Acetone-Butanol Continuous Flash Extractive Fermentation Process, Bioprocess Biosyst. Eng. 27:175-183, 2005.

Lynd, et al., Microbial Cellulose Utilization: Fundamentals and Biotechnology, Microbiology and Molecular Biology Reviews, 2002, 506-577, 66, 3, American Society for Microbiology.

Null, Phase Equilibrium in Process Design, Wiley-Interscience Publisher, 1970, 124-126.

Mariano, et al., An Alternative Process for Butanol Production: Continuous Flash Fermentation, Chemical Product and Process Modeling: vol. 3: Issue 1, Article 34, 2008.

Mariano, et al., Dynamics of a Continuous Flash Fermentation for Butanol Production, Chem. Eng. Transactions, 20:285-290, 2010.

Cysewski, et al., Rapid Ethanol Fermentation Using Vacuum and Cell Recycle, Biotech. Bioeng. 19:1125-1143, 1977.

Maiorella, et al. Low-Cost, Low-Energy Flash Ethanol Fermentation, Chemical Process Research and Development, Energy and Environment Division Annual Report, 1980, pp. 4-9 to 4-14.

Liu, et al. Downstream Process Synthesis for Biochemical Production of Butanol, Ethanol, and Acetone from Grains: Generation of Optimal and Near-optimal Flowsheets with Conventional Operating Units, Biotechnol. Prog. 20:1518-1527, 2004.

U.S. Appl. No. 13/193,147, filed Jul. 28, 2011.

U.S. Appl. No. 61/380,563, filed Jul. 9, 2010.

U.S. Appl. No. 61/379,546, filed Sep. 2, 2010.

International Search Report and Written Opinion of corresponding PCT/US2011/001409 mailed Mar. 21, 2012.

* cited by examiner

FIG. 7B
Table 8A: Results of Example 7

| Stream Labels | 23MASH (123) | 24BEER (119) | 67VENT (212) | 112VAP (122) | 113BEER (124) | 114BEER (114) | 115BEER (214) | 116REC (116) | AQUEOUS (546) |
|---|---|---|---|---|---|---|---|---|---|
| Mass Flow kg/hr | | | | | | | | | |
| Total | 228554 | 169327 | 45731 | 13474 | 5271890 | 5271890 | 5226160 | 5056800 | 30422 |
| Liquid/Vapor | 217451 | 158224 | 45731 | 13474 | 4929200 | 4929200 | 4883470 | 4725220 | 30422 |
| Solids | 11103 | 11103 | 0 | 0 | 342686 | 342686 | 342686 | 331583 | 0 |
| Temperature C | 32.2 | 28.0 | 28.0 | 29.7 | 28.0 | 31.4 | 28.0 | 28.0 | 40.0 |
| Pressure atm | 2.7 | 1.1 | 0.1 | 1.1 | 0.1 | 1.1 | 0.1 | 1.1 | 1.0 |
| Vapor Frac | 0.000 | 0.000 | 1.000 | 1.000 | 0.007 | 0.000 | 0.000 | 0.000 | 0.000 |
| Component Flows kg/hr | | | | | | | | | |
| i-BuOH | 595.747 | 3528.074 | 14535.94 | 148.648 | 123427.1 | 123427.1 | 108891.2 | 105352.8 | 2038.059 |
| H2O | 162239.4 | 142968.282 | 23298.54 | 245.527 | 4435900 | 4435900 | 4412600 | 4269610 | 28339.63 |
| Glucose | 44910.61 | 0 | 0 | 0 | 0 | 0 | 0 | 0 | 0 |
| NFDS | 6584.384 | 7965.422 | 0 | 0 | 245846.4 | 245846.4 | 245846.4 | 237880.8 | 0 |
| Protein | 3075.19 | 3759.807 | 0 | 0 | 116043.4 | 116043.4 | 116043.4 | 112283.5 | 0 |
| CO2 | 45.549 | 1.319 | 7896.482 | 13080.04 | 7937.179 | 7937.179 | 40.697 | 39.378 | 43.971 |
| EG | 0.005 | 0.005 | 0 | 0 | 0.163 | 0.163 | 0.163 | 0.158 | 0 |
| K+ | 0 | 0 | 0 | 0 | 0 | 0 | 0 | 0 | 0 |
| HCO3- | 0.296 | 1.182 | 0 | 0 | 36.471 | 36.471 | 36.471 | 35.29 | 0 |
| CO3-2 | 0 | 0 | 0 | 0 | 0 | 0 | 0 | 0 | 0 |
| Mass Frac | | | | | | | | | |
| i-BuOH | 0.003 | 0.022 | 0.318 | 0.011 | 0.025 | 0.025 | 0.022 | 0.022 | 0.067 |
| H2O | 0.746 | 0.904 | 0.509 | 0.018 | 0.9 | 0.9 | 0.904 | 0.904 | 0.932 |
| Glucose | 0.207 | 0 | 0 | 0 | 0 | 0 | 0 | 0 | 0 |
| NFDS | 0.03 | 0.05 | 0 | 0 | 0.05 | 0.05 | 0.05 | 0.05 | 0 |
| Protein | 0.014 | 0.024 | 0 | 0 | 0.024 | 0.024 | 0.024 | 0.024 | 0 |
| CO2 | 0 | 0 | 0.173 | 0.971 | 0.002 | 0.002 | 0 | 0 | 0.001 |
| EG | 0 | 0 | 0 | 0 | 0 | 0 | 0 | 0 | 0 |
| K+ | 0 | 0 | 0 | 0 | 0 | 0 | 0 | 0 | 0 |
| HCO3- | 0 | 0 | 0 | 0 | 0 | 0 | 0 | 0 | 0 |
| CO3-2 | 0 | 0 | 0 | 0 | 0 | 0 | 0 | 0 | 0 |
| Solids Flows kg/hr | | | | | | | | | |
| Starch | 408.28 | 408.276 | | | 12601.12 | 12601.12 | 12601.12 | 12192.84 | 0 |
| C5Poly | 3089.605 | 3089.595 | | | 95357.87 | 95357.87 | 95357.87 | 92268.27 | 0 |
| C6Poly | 1782.464 | 1782.459 | | | 55014.16 | 55014.16 | 55014.16 | 53231.69 | 0 |
| Protein | 3446.098 | 3446.087 | | | 106360.7 | 106360.7 | 106360.7 | 102914.6 | 0 |
| Oil | 2376.619 | 2376.612 | | | 73352.21 | 73352.21 | 73352.21 | 70975.59 | 0 |

FIG. 7C
Table 8B: Results of Example 7

| Stream Labels | BuOH (548) | COLVENT (442) | CONDENSE (444) | LEAN (320) | LEAN1 (432) | RICH (322') | RICH1B (324) | RICH3 (323) | VAPOR (440) | YEAST (121) |
|---|---|---|---|---|---|---|---|---|---|---|
| Mass Flow kg/hr | | | | | | | | | | |
| Total | 35960 | 8635 | 66381 | 500670 | 505826 | 6546410 | 6000000 | 546405 | 45000 | 8 |
| Liquid/Vapor | 35960 | 8635 | 66381 | 500670 | 505826 | 6546410 | 6000000 | 546405 | 45000 | 8 |
| Solids | 0 | 0 | 0 | 0 | 0 | 0 | 0 | 0 | 0 | 0 |
| Temperature C | 40.0 | 40.0 | 40.0 | 30.0 | 153.9 | 41.2 | 36.5 | 132.9 | 91.0 | 25.0 |
| Pressure atm | 1.0 | 1.0 | 1.0 | 1.0 | 1.1 | 0.1 | 1.0 | 2.0 | 1.0 | 1.0 |
| Vapor Frac | 0.000 | 1.000 | 0.000 | 0.000 | 0.000 | 0.000 | 0.000 | 0.001 | 1.000 | 0.000 |
| Component Flows kg/hr | | | | | | | | | | |
| i-BuOH | 29719.46 | 434.788 | 31757.52 | 0 | 0.089 | 174187.3 | 159648.53 | 14538.8 | 15977.89 | 0 |
| H2O | 6046.044 | 311.628 | 34385.68 | 49640.08 | 54760.61 | 835165.9 | 765454.45 | 69828.48 | 21093.5 | 8.484 |
| Glucose | 0 | 0 | 0 | 0 | 0 | 0 | 0 | 0 | 0 | 0 |
| NFDS | 0 | 0 | 0 | 0 | 0 | 0 | 0 | 0 | 0 | 0 |
| Protein | 0 | 0 | 0 | 0 | 0 | 0 | 0 | 0 | 0 | 0 |
| CO2 | 194.033 | 7888.228 | 238.004 | 0.007 | 0.853 | 41.911 | 30.614 | 298.701 | 7928.613 | 0 |
| EG | 0 | 0 | 0 | 399864.1 | 399865.2 | 4790730 | 4390860 | 399865.3 | 0 | 0 |
| K+ | 0 | 0 | 0 | 28282.94 | 28281.87 | 338841.1 | 310559.24 | 28281.87 | 0 | 0 |
| HCO3- | 0 | 0 | 0 | 2322.201 | 2420.673 | 290072.5 | 265882.63 | 28395.17 | 0 | 0 |
| CO3-2 | 0 | 0 | 0 | 20560.48 | 20477.36 | 117366.7 | 107560.03 | 10196.34 | 0 | 0 |
| Mass Frac | | | | | | | | | | |
| i-BuOH | 0.826 | 0.05 | 0.478 | 0 | 0 | 0.027 | 0.027 | 0.027 | 0.355 | 0 |
| H2O | 0.168 | 0.036 | 0.518 | 0.099 | 0.108 | 0.128 | 0.128 | 0.128 | 0.469 | 1 |
| Glucose | 0 | 0 | 0 | 0 | 0 | 0 | 0 | 0 | 0 | 0 |
| NFDS | 0 | 0 | 0 | 0 | 0 | 0 | 0 | 0 | 0 | 0 |
| Protein | 0 | 0 | 0 | 0 | 0 | 0 | 0 | 0 | 0 | 0 |
| CO2 | 0.005 | 0.914 | 0.004 | 0 | 0 | 0 | 0 | 0.001 | 0.176 | 0 |
| EG | 0 | 0 | 0 | 0.799 | 0.791 | 0.732 | 0.732 | 0.732 | 0 | 0 |
| K+ | 0 | 0 | 0 | 0.056 | 0.056 | 0.052 | 0.052 | 0.052 | 0 | 0 |
| HCO3- | 0 | 0 | 0 | 0.005 | 0.005 | 0.044 | 0.044 | 0.043 | 0 | 0 |
| CO3-2 | 0 | 0 | 0 | 0.041 | 0.04 | 0.018 | 0.018 | 0.019 | 0 | 0 |
| Solids Flows kg/hr | | | | | | | | | | |
| Starch | 0 | | | 0 | | 0 | | 0 | 0 | 0 |
| C5Poly | 0 | | | 0 | | 0 | | 0 | 0 | 0 |
| C6Poly | 0 | | | 0 | | 0 | | 0 | 0 | 0 |
| Protein | 0 | | | 0 | | 0 | | 0 | 0 | 0 |
| Oil | 0 | | | 0 | | 0 | | 0 | 0 | 0 |

FIG. 8B
Table 10A: Results of Example 8

| Stream Labels | 324 | 328 | 322' | 323 | 320 | 440 | 432 | 23MASH (123) | 26BEER (124) | 28RCY (128) | 29BEER (129) |
|---|---|---|---|---|---|---|---|---|---|---|---|
| Mass Flow kg/hr | | | | | | | | | | | |
| Total | 2000000 | 21328 | 2438950 | 438945 | 400000 | 43805 | 399783 | 780968 | 760279 | 552563 | 225695 |
| Liquid/Vapor | 2000000 | 21328 | 2438950 | 438945 | 400000 | 43805 | 399783 | 742743 | 722055 | 525423 | 214610 |
| Solids | 0 | 0 | 0 | 0 | 0 | 0 | 0 | 38224 | 38224 | 27139 | 11085 |
| Temperature C | 30.0 | 37.7 | 40.9 | 40.9 | 40.0 | 97.3 | 113.4 | 42.6 | 34.3 | 46.4 | 46.4 |
| Pressure atm | 1.00 | 0.05 | 0.06 | 0.06 | 1.00 | 1.00 | 1.10 | 1.09 | 0.07 | 1.09 | 1.09 |
| Vapor Frac | 0.000 | 1.000 | 0.000 | 0.000 | 0.000 | 1.000 | 0.000 | 0.000 | 0.006 | 0.000 | 0.000 |
| Component Flows kg/hr | | | | | | | | | | | |
| i-BuOH | 60092.292 | 7588.781 | 73281.14 | 13188.647 | 0 | 13492.28 | 39.978 | 496.321 | 17894.99 | 149.011 | 60.864 |
| Water | 846745.41 | 12691.15 | 1032580 | 185837.27 | 160000 | 30311.71 | 159817.63 | 660397.6 | 664322.5 | 497627.9 | 203257 |
| Glucose | 0 | 0 | 0 | 0 | 0 | 0 | 0 | 45017.77 | 0 | 0 | 0 |
| NFDS | 0 | 0 | 0 | 0 | 0 | 0 | 0 | 19035.7 | 18533.51 | 13159.08 | 5374.719 |
| Protein | 0 | 0 | 0 | 0 | 0 | 0 | 0 | 17559.72 | 20132.72 | 14293.63 | 5838.49 |
| CO2 | 0 | 967.06 | 1.012 | 0.182 | 0 | 0.645 | 0 | 28.185 | 963.073 | 0 | 0 |
| EG | 1093160 | 81.225 | 1333080 | 239918.85 | 240000 | 0.788 | 239924.93 | 207.974 | 207.973 | 193.843 | 79.173 |
| Mass Frac | | | | | | | | | | | |
| i-BuOH | 0.03 | 0.356 | 0.03 | 0.03 | 0 | 0.308 | 0 | 0.001 | 0.025 | 0 | 0 |
| Water | 0.423 | 0.595 | 0.423 | 0.423 | 0.4 | 0.692 | 0.4 | 0.889 | 0.92 | 0.947 | 0.947 |
| Glucose | 0 | 0 | 0 | 0 | 0 | 0 | 0 | 0.061 | 0 | 0 | 0 |
| NFDS | 0 | 0 | 0 | 0 | 0 | 0 | 0 | 0.026 | 0.026 | 0.025 | 0.025 |
| Protein | 0 | 0 | 0 | 0 | 0 | 0 | 0 | 0.024 | 0.028 | 0.027 | 0.027 |
| CO2 | 0 | 0.045 | 0 | 0 | 0 | 0 | 0 | 0 | 0.001 | 0 | 0 |
| EG | 0.547 | 0.004 | 0.547 | 0.547 | 0.6 | 0 | 0.6 | 0 | 0 | 0 | 0 |
| Solids Flows kg/hr | | | | | | | | | | | |
| Starch | 0 | 0 | 0 | 0 | 0 | 0 | 0 | 1411.207 | 1411.207 | 1001.953 | 409.25 |
| C5Poly | 0 | 0 | 0 | 0 | 0 | 0 | 0 | 10634.95 | 10634.95 | 7550.766 | 3084.136 |
| C6Poly | 0 | 0 | 0 | 0 | 0 | 0 | 0 | 6135.543 | 6135.543 | 4356.204 | 1779.307 |
| Protein | 0 | 0 | 0 | 0 | 0 | 0 | 0 | 11862.05 | 11862.05 | 8422 | 3439.996 |
| Oil | 0 | 0 | 0 | 0 | 0 | 0 | 0 | 8180.729 | 8180.729 | 5808.278 | 2372.411 |

FIG. 8C

Table 10B: Results of Example 8

| Stream Name | 30BOV (212) | 32COND (844a) | 34VAP (342) | 40VAP (344) | 38COND (844b) | 47ORG (548) | 48AQ (546) | 68CO2 (122') | YEAST (121') |
|---|---|---|---|---|---|---|---|---|---|
| Mass Flow kg/hr | | | | | | | | | |
| Total | 60273 | 6060 | 15268 | 1003 | 14265.57 | 40155 | 46430 | 20697 | 8 |
| Liquid / Vapor | 60273 | 6060 | 15268 | 1003 | 14265.57 | 40155 | 46430 | 20697 | 8 |
| Solids | 0 | 0 | 0 | 0 | 0.00 | 0 | 0 | 0 | 0 |
| Temperature C | 36.5 | 30.0 | 30.0 | 30.0 | 30 | 40.0 | 40.0 | 32.2 | 25.0 |
| Pressure atm | 0.07 | 0.06 | 0.06 | 1.09 | 1.09 | 1.09 | 1.09 | 1.09 | 1.09 |
| Vapor Frac | 1.000 | 0.000 | 1.000 | 1.000 | 0.00 | 0.000 | 0.000 | 1.000 | 0.000 |
| Component Flows kg/hr | | | | | | | | | |
| I-BUOH | 20777.63 | 235.761 | 7353.02 | 22.409 | 7330.61 | 32875.52 | 3436.103 | 270.62 | 0 |
| WATER | 38528.23 | 5743.455 | 6947.694 | 16.040 | 6931.66 | 7263.215 | 42920.66 | 378.376 | 0 |
| GLUCOSE | 0 | 0 | 0 | 0 | 0.00 | 0 | 0 | 0 | 0 |
| NFDS | 0 | 0 | 0 | 0 | 0.00 | 0 | 0 | 0 | 0 |
| PROTEIN | 0 | 0 | 0 | 0 | 0.00 | 0 | 0 | 0 | 8.484 |
| CO2 | 967.242 | 0.021 | 0.963 | 963.073 | 3.97 | 2.641 | 4.632 | 20047.99 | 0 |
| EG | 0.066 | 80.875 | 0.349 | 0 | 0.35 | 13.469 | 68.671 | 0 | 0 |
| Mass Frac | | | | | | | | | |
| I-BUOH | 0.345 | 0.039 | 0.482 | 0.023 | 1.101 | 0.819 | 0.074 | 0.013 | 0 |
| WATER | 0.639 | 0.948 | 0.456 | 0.016 | 0.898 | 0.181 | 0.924 | 0.018 | 1 |
| GLUCOSE | 0 | 0 | 0 | 0 | 0 | 0 | 0 | 0 | 0 |
| NFDS | 0 | 0 | 0 | 0 | 0 | 0 | 0 | 0 | 0 |
| PROTEIN | 0 | 0 | 0 | 0 | 0 | 0 | 0 | 0 | 0 |
| CO2 | 0.016 | 0 | 0.063 | 0.961 | 0.001 | 0 | 0 | 0.969 | 0 |
| EG | 0 | 0.013 | 0 | 0 | 0 | 0.001 | 0.001 | 0 | 0 |
| Solids Flows kg/hr | | | | | | | | | |
| STARCH | 0 | 0 | 0 | 0 | 0 | 0 | 0 | 0 | 0 |
| C5POLY | 0 | 0 | 0 | 0 | 0 | 0 | 0 | 0 | 0 |
| C6POLY | 0 | 0 | 0 | 0 | 0 | 0 | 0 | 0 | 0 |
| PROTEIN | 0 | 0 | 0 | 0 | 0 | 0 | 0 | 0 | 0 |
| OIL | 0 | 0 | 0 | 0 | 0 | 0 | 0 | 0 | 0 |

FIG. 9B

Table 12A. Results of Example 9

| Stream Name | 23MASH (123) | 26BEER (126) | 27BOT (127) | 28RCY (128) | 29BEER (129) | 30BOV (130) | 32COND (132) | 34VAP (134) |
|---|---|---|---|---|---|---|---|---|
| Mass Flow kg/hr | | | | | | | | |
| Total | 779201 | 758660 | 776236 | 551115 | 225108 | 60086 | 53706 | 6381 |
| Liquid / Vapor | 741063 | 720422 | 738097 | 524037 | 214048 | 60086 | 53706 | 6381 |
| Solids | 38138 | 38138 | 38138 | 27078 | 11060 | 0 | 0 | 0 |
| Temperature C | 42.6 | 34.3 | 46.4 | 46.4 | 46.4 | 36.5 | 30.0 | 30.0 |
| Pressure atm | 1.09 | 0.07 | 1.09 | 1.09 | 1.09 | 0.07 | 0.07 | 0.07 |
| Vapor Frac | 0.000 | 0.006 | 0.000 | 0.000 | 0.000 | 1.000 | 0.000 | 1.000 |
| Component Flows kg/hr | | | | | | | | |
| WATER | 494.992 | 17851.336 | 209.113 | 148.472 | 60.643 | 20702.29 | 17227.42 | 3474.867 |
| GLUCOSE | 659100.78 | 660016.551 | 669297.2 | 496488.7 | 202796.2 | 39420.25 | 36476.5 | 1943.758 |
| NFDS | 44913.622 | 0 | 0 | 0 | 0 | 0 | 0 | 0 |
| PROTEIN | 19001.332 | 18500.167 | 18500.17 | 13136.06 | 5365.048 | 0 | 0 | 0 |
| CO2 | 1752.376 | 20090.951 | 20090.96 | 14263.94 | 5826.376 | 0 | 0 | 0 |
|  | 28.441 | 961.088 | 0 | 0 | 0 | 963.663 | 1.109 | 962.554 |
| Mass Frac | | | | | | | | |
| I-BUOH | 0.001 | 0.025 | 0 | 0 | 0 | 0.345 | 0.321 | 0.545 |
| WATER | 0.889 | 0.92 | 0.947 | 0.947 | 0.947 | 0.639 | 0.679 | 0.305 |
| GLUCOSE | 0.061 | 0 | 0 | 0 | 0 | 0 | 0 | 0 |
| NFDS | 0.026 | 0.026 | 0.025 | 0.025 | 0.025 | 0 | 0 | 0 |
| PROTEIN | 0.024 | 0.028 | 0.027 | 0.027 | 0.027 | 0 | 0 | 0 |
| CO2 | 0 | 0.001 | 0 | 0 | 0 | 0.016 | 0.151 | 0 |
| Solids Flows kg/hr | | | | | | | | |
| STARCH | 1407.986 | 1407.986 | 1407.986 | 999.679 | 408.316 | 0 | 0 | 0 |
| C5POLY | 10610.997 | 10610.997 | 10611 | 7533.887 | 3077.189 | 0 | 0 | 0 |
| C6POLY | 6121.451 | 6121.451 | 6121.451 | 4346.196 | 1775.221 | 0 | 0 | 0 |
| PROTEIN | 11834.994 | 11834.994 | 11834.99 | 8402.834 | 3432.148 | 0 | 0 | 0 |
| OIL | 8162.151 | 8162.151 | 8162.151 | 5795.144 | 2367.024 | 0 | 0 | 0 |

FIG. 9C

Table 12B: Results of Example 9

| Stream Name | 37COND (137) | 40VAP (140) | 43COND (143) | YEAST (121) |
|---|---|---|---|---|
| Mass Flow kg/hr | | | | |
| Total | 5236 | 100 | 145 | 8 |
| Liquid / Vapor | 5236 | 1000 | 145 | 8 |
| Solids | 0 | 0 | 0 | 0 |
| Temperature C | 30.0 | 30.0 | 30.0 | 25.0 |
| Pressure atm | 0.27 | 1.09 | 1.09 | 1.00 |
| Vapor Frac | 0.000 | 1.000 | 0.000 | 0.000 |
| Component Flows kg/hr | | | | |
| I-BUOH | 3368.172 | 23.361 | 85.334 | 0 |
| WATER | 1868.075 | 16.016 | 59.664 | 8.484 |
| GLUCOSE | 0 | 0 | 0 | 0 |
| NFDS | 0 | 0 | 0 | 0 |
| PROTEIN | 0 | 0 | 0 | 0 |
| CO2 | 1.289 | 961.098 | 0.176 | 0 |
| Mass Frac | | | | |
| I-BUOH | 0.643 | 0.023 | 0.588 | 0 |
| WATER | 0.357 | 0.016 | 0.411 | 1 |
| GLUCOSE | 0 | 0 | 0 | 0 |
| NFDS | 0 | 0 | 0 | 0 |
| PROTEIN | 0 | 0 | 0 | 0 |
| CO2 | 0 | 0.961 | 0.001 | 0 |
| Solids Flows kg/hr | | | | |
| STARCH | 0 | 0 | 0 | 0 |
| C6POLY | 0 | 0 | 0 | 0 |
| C5POLY | 0 | 0 | 0 | 0 |
| PROTEIN | 0 | 0 | 0 | 0 |
| OIL | 0 | 0 | 0 | 0 |

Fig. 10 B
Table 14A: Results from Example 10

| Stream | 125 | 414 | 122 | 415 | 124 | 220 |
|---|---|---|---|---|---|---|
| All phases | | | | | | |
| Total Flow kg/hr | 2.26E+06 | 2.07E+06 | 1574.72 | 1.53E+05 | 2.09E+06 | 2308.027 |
| Vapor/Liquid | | | | | | |
| Mass Flow kg/hr | | | | | | |
| N2 | 4.58E-04 | | 4.56E-04 | 1.18E-07 | 1.40E-06 | 1770.447 |
| O2 | 5.33E-04 | | 5.29E-04 | 2.68E-07 | 3.32E-06 | 537.5798 |
| CO2 | 0.2071568 | | 15290.02 | 183.3877 | 2261.781 | 0 |
| Water | 1.74E+06 | | 304.8889 | 1.31E+05 | 1.62E+06 | 0 |
| 1-BuOH | 3265.46 | | 147.5398 | 2379.718 | 45214.66 | 0 |
| Glucose | 3773.22 | | 0 | 0 | 0 | 0 |
| Starch | 1.92E+05 | | 4.40E-11 | 0 | 1.92E+05 | 0 |
| Total Flow kg/hr | 2.19E+06 | | 1574.72 | 1.47E+05 | 2.02E+06 | 2308.027 |
| Temperature °C | 31.97486 | | 32 | 32 | 32 | 32 |
| Pressure atm | 1 | | 1 | 1 | 1 | 1 |
| Vapor Frac | 0 | | 1 | 2.86E-05 | 0 | 1 |
| Liquid Frac | 1 | | 0 | 0.9999714 | 1 | 0 |
| Solids | | | | | | |
| Total Flow kg/hr | 72144.95 | | 0 | 5461.128 | 67353.92 | 0 |

Fig. 10 C
Table 14B: Results from Example 10

| Stream | 222 | 124 | 330 | 323 | 428 |
|---|---|---|---|---|---|
| All phases | | | | | |
| Total Flow kg/hr | 4551.233 | 2.09E+06 | 64465.51 | 14880.1 | 400.8849 |
| Vapor/Liquid | | | | | |
| Mass Flow kg/hr | | | | | |
| N2 | 1747.31 | 23.13701 | 23.14225 | 0.0142348 | 23.12232 |
| O2 | 523.8349 | 13.74497 | 13.75126 | 0.0155542 | 13.72888 |
| CO2 | 2115.515 | 146.2666 | 147.9585 | 1.8144 | 144.3154 |
| Water | 110.4441 | 1.62E+06 | 46947.02 | 2544.992 | 93.41913 |
| i-BuOH | 54.07154 | 45160.58 | 17310.63 | 12328.15 | 126.2883 |
| Glucose | 0 | 0 | 0 | 0 | 0 |
| Starch | 1.59E-11 | 1.92E+05 | 6.16E-09 | 1.00E-09 | 3.61E-24 |
| Total Flow kg/hr | 4551.233 | 2.02E+06 | 64465.51 | 14880.1 | 400.8849 |
| Temperature ºC | 31.91517 | 31.84839 | 32.02931 | 20.03983 | 20 |
| Pressure atm | 1 | 1 | 0.05 | 0.5 | 1 |
| Vapor Frac | 1 | 0 | 1 | 0 | 1 |
| Liquid Frac | 0 | 1 | 0 | 1 | 0 |
| Solids | | | | | |
| Total Flow kg/hr | 0 | 67353.92 | 0 | 0 | 0 |

PROCESS TO REMOVE PRODUCT ALCOHOL FROM A FERMENTATION BY VAPORIZATION UNDER VACUUM

CROSS-REFERENCE TO RELATED APPLICATIONS

This application claims the benefit of U.S. Provisional Application No. 61/379,546, filed on Sep. 2, 2010; U.S. Provisional Application No. 61/427,896, filed Dec. 29, 2010; U.S. Provisional Application No. 61/440,034, filed on Feb. 7, 2011; U.S. patent application Ser. No. 13/023,134, filed on Feb. 8, 2011; U.S. patent application Ser. No. 13/162,868, filed on Jun. 17, 2011; and U.S. patent application Ser. No. 13/193,147, filed on Jul. 28, 2011, the entire disclosures of which are incorporated in their entirety herein by reference thereto.

FIELD OF THE INVENTION

The present invention relates to processes to remove butanol and other $C_2$ to $C_8$ alcohols from a fermentation broth employing vacuum vaporization.

BACKGROUND

Currently, much industrial fermentation involves the manufacture of ethanol for either chemical or fuels use. For use in fuel, butanol has advantages as compared to ethanol, namely butanol has a lower vapor pressure and decreased solubility in water.

An advantageous butanol fermentation process would encompass a complete, or substantially complete, conversion of sugars to butanol without reaching a butanol titer above a threshold of butanol tolerance that causes the rate of butanol production to fall below an undesirable predetermined rate. While it may be possible to limit sugar loadings to a level whereby batch fermentation does not require operation at a butanol concentration above the tolerance level, this approach has disadvantages because limited sugar loadings result in dilute solutions that are themselves economically undesirable to process. Therefore, there is a need for a process by which levels of butanol are limited in a fermentation at or below the tolerance level while sugar loadings are not limited by considerations of the tolerance level.

One means by which a butanol producing fermentation process might be made more efficient would be to remove the butanol as it is being formed from the fermentation medium (broth), so that the tolerance level of the butanol producing microorganism is not reached, allowing high loading of sugar to be charged to the fermentation vessel. Such an "in situ product removal" or "ISPR" process is described in PCT International Publication No. WO2009/079362 A2.

ISPR processes for fermentation products are also described in the Roffler dissertation (Roffler, Steve Ronald, "Extractive fermentation—lactic acid and acetone/butanol production," Department of Chemical Engineering at the University of California at Berkeley, 1986). Roffler describes a process whereby a liquid stream from a fermentation vessel is passed to a separate vessel which is held under vacuum. However, the method described in Roffler necessitates further processing of the resulting vapor stream. Because an industrial fermentation relies on microorganisms, such processing must consider temperature constraints relative to the microorganisms.

To operate at acceptable temperatures, consideration must be given to costs and practicalities of cooling or operation under vacuum. The costs associated with removal of heat within a chemical process can be a function of the plant location and also the time of the year. In many geographic areas, it is not possible to guarantee cooling to be available or practical at the temperature at which heat needs to be removed from the vapor stream.

Providing chilled water to the heat exchanger by which condensation is carried out significantly increases the cost of the cooling medium. An alternative would be to compress the vapor stream to a higher pressure to allow the condensation to be done against cooling water year round, but this too entails significant cost because of the low density of the initial vapor passing to the machine. Processes described which use lithium bromide for absorption of ethanol and water vapors may not be adequate for absorbing carbon dioxide or higher alcohols of a vapor stream.

In addition, with whatever method is used, there will be a residual gas stream (due to the solubility of $CO_2$ in the fermentation broth) that must be compressed before discharge to the atmosphere. The residual gas stream will comprise $CO_2$. While vacuum flashing represents an effective means by which butanol can be removed from a fermentation process, there is a need for advances in the processing of the resulting low pressure vapor stream containing the product.

SUMMARY OF THE INVENTION

Methods of removing product alcohol from a fermentation by vaporization under vacuum are presented. For example, in some embodiments, a fermentation liquid feed comprising water and a product alcohol and optionally $CO_2$ is at least partially vaporized such that a vapor stream is produced. Methods of recovering a product alcohol from the vaporized fermentation feed are also presented. For example, in some embodiments, the vapor stream containing the product alcohol is contacted with an absorption liquid under suitable conditions wherein an amount of the product alcohol is absorbed. Also presented are methods of recovering a product alcohol from the absorption liquid whereby the absorption liquid is regenerated.

In some embodiments, a method includes at least partially vaporizing a fermentation liquid feed wherein a vapor stream is produced, the fermentation liquid feed and the vapor stream each including an amount of each water, a product alcohol, and optionally $CO_2$; and contacting the vapor stream with an absorption liquid under vacuum conditions wherein at least a portion of the vapor stream is absorbed into the absorption liquid to form an absorption liquid phase. The portion of the vapor stream that is absorbed can include an amount of each of the water, the product alcohol, and optionally the $CO_2$. The temperature at the onset of the absorption of the vapor stream into the absorption liquid can be greater than the temperature at the onset of condensation of the vapor stream in the absence of the absorption liquid.

In some embodiments, partially vaporizing the fermentation liquid can include removing the fermentation liquid feed from a fermentation vessel; supplying the fermentation liquid feed to a distillation column (e.g., a multi-stage distillation column) at a suitable flow rate; distilling the fermentation liquid feed to produce the vapor stream enriched in the product alcohol and a bottoms stream depleted in the product alcohol, wherein the distilling occurs under a pressure sufficiently below atmospheric to allow for the vapor stream to be produced at a temperature no greater than about 45° C.; and optionally, returning any portion of the bottoms stream to the fermentation vessel. In some embodiments, the concentration of the product alcohol in the bottoms stream is not more than 90% of the concentration of the product alcohol in the fermentation liquid feed. In some embodiments, the (a) vaporizing and the (b) contacting are carried out at a pressure of less than about 0.2 bar. In some embodiments, the (a) vaporizing and the (b) contacting are carried out at a pressure of less than about 0.1 bar. In some embodiments, at least about 90% of the vapor stream is absorbed into the absorption liquid phase. In some embodiments, the temperature at the onset of the absorption of the vapor stream into the absorption liquid is at least about 10° C. greater than the temperature at the onset of condensation of the vapor stream in the absence of the absorption liquid. In some embodiments, the temperature at the onset of the absorption of the vapor stream into the absorption liquid phase is at least about 30° C. In some embodiments, the product alcohol is butanol. In some embodiments, the product alcohol is isobutanol. In some embodiments, the absorption liquid comprises a organic molecule with a boiling point at least about 30° C. greater than the boiling point of water at atmospheric pressure. In some embodiments, the absorption liquid comprises potassium carbonate and ethylene glycol. In some embodiments, the absorption liquid comprises glycol. In some embodiments, the glycol comprises ethylene glycol, propylene glycol, or a mixture thereof. In some embodiments, the absorption liquid comprises ethylene glycol. In some embodiments, the organic molecule is an amine. In some embodiments, the amine is selected from the group consisting of monoethanolamine (MEA), 2-amino 2-methyl propanol (AMP), and methyldiethanolamine (MDEA). In some embodiments, the absorption liquid comprises MEA, AMP, MDEA, or any mixture thereof. In some embodiments, the absorption liquid comprises MEA. In some embodiments, the absorption liquid comprises AMP. In some embodiments, the absorption liquid comprises MDEA. In some embodiments, the absorption liquid comprises a mixture of at least two of MEA, AMP, and MDEA. In some embodiments, the molar ratio of absorption liquid to $CO_2$ in the vapor stream is greater than about 1. In some embodiments, the method further comprises distilling the absorption liquid phase containing the absorbed vapor stream under conditions sufficient to remove a substantial portion of the water, the product alcohol, and the $CO_2$ from the absorption liquid. In some embodiments, a substantial portion of the $CO_2$ and at least a portion of at least one of the product alcohol and the water or both are absorbed into the absorption liquid. In some embodiments, a substantial portion of each of the $CO_2$, the product alcohol, and the water are absorbed into the absorption liquid. In some embodiments, a substantial portion of the product alcohol and at least a portion of the $CO_2$ and the water are absorbed into the absorption liquid. In some embodiments, a substantial portion of the product alcohol and the $CO_2$ and at least a portion of the water are absorbed into the absorption liquid. In some embodiments, a substantial portion of the product alcohol and the water and at least a portion of the $CO_2$ are absorbed into the absorption liquid. In some embodiments, the method further comprises, prior to the (a) vaporizing step, one or both of (i) gas stripping a portion of the $CO_2$ from the fermentation liquid feed and (ii) vaporizing a portion of the $CO_2$ from the fermentation liquid feed. In some embodiments, the method further comprises, prior to the (a) vaporizing step, one or both of (i) gas stripping a substantial portion of the $CO_2$ and a portion of product alcohol from the fermentation liquid feed and (ii) vaporizing a portion of the $CO_2$ from the fermentation liquid feed. In some embodiments, a portion of the $CO_2$ from the fermentation liquid feed is gas stripped from the fermentation liquid feed prior to the (a) vaporizing step, where the portion of the $CO_2$ is gas stripped by counter-current contact of the fermentation liquid feed with a noncondensible gas.

In some embodiments, a titer of product alcohol in a fermentation vessel can be maintained below a preselected threshold pursuant to methods presented herein. For example, a method can include removing from a fermentation vessel a fermentation liquid feed stream comprising product alcohol, water, and optionally $CO_2$; supplying the fermentation liquid feed stream to a flash tank (e.g., a single-stage flash tank) or a distillation column (e.g., multi-stage distillation column); vaporizing under vacuum conditions the fermentation liquid feed stream in the flash tank (e.g., a single-stage flash tank) or the distillation column (e.g., multi-stage distillation column) to produce a vapor stream enriched in product alcohol and a bottoms stream depleted in product alcohol; and optionally returning any portion of the bottoms stream to the fermentation vessel. In some embodiments, the vapor stream is contacted with an absorption liquid under vacuum conditions wherein at least a portion of the vapor stream is absorbed into the absorption liquid. In some embodiments, the temperature at the onset of the absorption of the vapor stream into the absorption liquid is greater than the temperature at the onset of condensation of the vapor stream in the absence of the absorption liquid. In some embodiments, the concentration of product alcohol in the bottoms stream is less than about 90% of the concentration of product alcohol in the fermentation liquid feed stream. In some embodiments, the concentration of product alcohol in the bottoms stream is less than about 10% of the concentration of product alcohol in the fermentation liquid feed stream. In some embodiments, the organic molecule is an amine. In some embodiments, the organic molecule is ethylene glycol. In some embodiments, the concentration of product alcohol of the bottoms stream is less than about 2.5 g/L. In some embodiments, the fermentation liquid feed stream comprises $CO_2$. In some embodiments, the method is initiated when the product alcohol in the fermentation vessel reaches about 10 g/L. In some embodiments, the method is initiated concurrently with initiation of the fermentation producing the fermentation liquid feed stream.

In some embodiments of the methods presented herein, the fermentation liquid feed includes $CO_2$. In some embodiments, the product alcohol is butanol. In some embodiments, the absorption liquid comprises an organic molecule different from the product alcohol. In some embodiments, the absorption liquid includes an organic molecule with a boiling point at least 30° C. greater than the boiling point of water. In some embodiments, the organic molecule is an amine such as monoethanolamine (MEA), 2-amino 2-methyl propanol (AMP), methyldiethanolamine (MDEA), or a mixture thereof. In some embodiments, the absorption liquid comprises potassium carbonate and ethylene glycol. In some embodiments, the absorption liquid comprises ethylene glycol. In some embodiments, the absorption liquid comprises ethylene glycol and an amine such as MEA, AMP, MDEA, and mixtures thereof. In some embodiments, the absorption liquid may comprise an organic molecule that exhibits a superior absorption affinity for isobutanol over water. In some embodiments, the absorption liquid comprises 2-ethyl hexanol (2-EH), isolauryl alcohol, phenol, and mixtures thereof. In some embodiments, the absorption liquid comprises a fatty acid, fatty ester, fatty alcohol, and mixtures thereof. The fatty acid, fatty ester, or fatty alcohol may be derived from corn oil, soybean oil, or castor oil.

In some embodiments, a substantial portion of the product alcohol and at least a portion of the CO2, water, or both are absorbed into absorption liquid. In some embodiments, a substantial portion of the product alcohol and water and at least a portion of $CO_2$ are absorbed. In some embodiments, a substantial portion of product alcohol and $CO_2$ and at least a portion of water are absorbed. In some embodiments, a substantial portion of product alcohol, water, and $CO_2$ are absorbed.

Also provided herein is a method of recovering a product alcohol from an absorption liquid and regenerating the absorption liquid. Recovering the product alcohol may include (a) pumping from an absorption device an absorption liquid phase including an absorption liquid, water, product alcohol, and optionally $CO_2$, to a higher pressure than a pressure in the absorption device; (b) optionally, heating the absorption liquid phase; (c) feeding the absorption liquid phase to a distillation column (e.g., multi-stage distillation column) comprising a stripping section and optionally a rectification section; (d) operating the distillation column under conditions such that a bottoms product comprising the absorption liquid and at least a portion of water, and a vapor phase comprising a mixture of water, product alcohol, and optionally $CO_2$ are produced; (e) recovering the bottoms product comprising a mixture of water and the absorption liquid phase from the distillation column; and (f) recovering the water, the product alcohol, and optionally $CO_2$ from the vapor phase. In some embodiments, the method further comprises causing to be separated the constituent parts of the vapor phase from (f) by condensation, distillation, decantation, or a combination thereof.

In some embodiments, the method further comprises (g) at least partially condensing the vapor phase produced in step (d) to form a two liquid phase mixture; (h) passing the liquid phase mixture to a decanter wherein the liquid phase mixture is separated into an aqueous phase and an organic phase; (i) optionally passing at least portion of the aqueous phase to the rectification section of the distillation column of step (c); (j) removing a liquid side stream from the rectification section of the distillation column and returning it to a vacuum flash vessel configured to receive a fermentation liquid feed stream comprising product alcohol, water, and optionally CO2; (k) passing at least a portion of the organic phase to a second distillation column comprising a stripping section; (l) withdrawing a product alcohol from a bottom of the second distillation column; (m) withdrawing vapors from a top of the second distillation column; (n) causing the vapors from (m) to be cooled so that the vapors partially condense to form two liquid phases; and (o) passing the liquid phases from (n) to a decanter. In some embodiments, the method further comprises substantially reducing the amount of carbon dioxide present in the fermentation liquid feed to vessel 210, by pre-flashing from the fermentation liquid at a pressure intermediate between atmospheric pressure and the pressure of the flash at vessel 210. In some embodiments, the method further comprises substantially reducing the amount of carbon dioxide present in the fermentation liquid feed to vessel 210, by non-condensible gas stripping prior to the flash vessel 210. In some embodiments, the product alcohol is butanol and a portion of the CO2 butanol and water are volatilized prior to beer stripping wherein said partial volatization provides improved process efficiency. In some embodiments, the vapor stream that is partially vaporized and the vapor stream absorbed into the absorption liquid are 1 to 100 parts by mass butanol to one part carbon dioxide. In some embodiments, the vapor streams are 10 to 100 parts by mass butanol to one part carbon dioxide. In some embodiments, the pressure of the vapor phase comprises 1 to 100 parts by mass butanol to one part carbon dioxide and the pressure is 1 to 30 psig. In some embodiments, the pressure is 0.9 to 1.2 atmospheres.

The present invention is also directed to a method for removing a product alcohol from a fermentation liquid, comprising: (a) at least partially vaporizing a fermentation liquid feed wherein a vapor stream is produced, the fermentation liquid feed and the vapor stream each comprising an amount of water, a product alcohol and CO2; and (b) contacting the vapor stream with an absorption liquid under vacuum conditions wherein at least a portion of the vapor stream is absorbed into the absorption liquid to form an absorption liquid phase, wherein the portion of the vapor stream that is absorbed includes an amount of each of the water, the product alcohol, and the CO2, and wherein the temperature at the onset of the absorption of the vapor stream into the absorption liquid is greater than the temperature at the onset of condensation of the vapor stream in the absence of the absorption liquid, and wherein the heat of absorption generated by the (b) contacting is used in the (a) at least partially vaporizing a fermentation liquid feed. In one embodiment, the (a) vaporizing comprises: (i) removing the fermentation liquid feed from a fermentation vessel; (ii) supplying the fermentation liquid feed to a distillation column at a flow rate; (iii) distilling the fermentation liquid feed to produce the vapor stream enriched in the product alcohol and a bottoms stream depleted in the product alcohol, wherein the distilling occurs under a pressure sufficiently below atmospheric to allow for the vapor stream to be produced at a temperature no greater than about 45° C.; and (iv) optionally, returning any portion of the bottoms stream to the fermentation vessel, wherein the concentration of the product alcohol in the bottoms stream is not more than about 90% of the concentration of the product alcohol in the fermentation liquid feed. In some embodiments, step (b) further comprises optionally forming a residual vapor phase. In some embodiments, the product alcohol is butanol. In some embodiments, the product alcohol is isobutanol. In some embodiments, the absorption liquid comprises ethylene glycol, ethylene glycol monomethyl ether, diethylene glycol, propylene glycol, dipropylene glycol, polyethylene glycols, polyethylene glycol ethers, polypropylene glycol ethers, and mixtures thereof. In some embodiments, the absorption liquid comprises monoethanolamine, methylaminopropylamine, piperazine, diethanolamine, triethanolamine, diethylethanolamine, diisopropylamine, aminoethoxyethanol, dimethylaminopropanol, methyldiethanolamine, and mixtures thereof. In some embodiments, the absorption liquid comprises 2-ethyl hexanol, isolauryl alcohol, isocetyl alcohol, oleyl alcohol, phenol, fatty acids, fatty esters, fatty alcohols, acids, alcohols, amides, amines, esters, ketones, carbonates, phosphates, salt solutions, and mixtures thereof. In some embodiments, the absorption liquid comprises potassium carbonate and ethylene glycol. In some embodiments, the method further comprises distilling the absorption liquid phase containing the absorbed vapor stream under conditions sufficient to remove a substantial portion of the water, the product alcohol, and the CO2 from the absorption liquid. In some embodiments, a substantial portion of the CO2 and at least a portion of at least one of the product alcohol and the water or both are absorbed into the absorption liquid. In some embodiments, a substantial portion of each of the CO2, the product alcohol, and the water are absorbed into the absorption liquid. In some embodiments, a substantial portion of the product alcohol and at least a portion of the CO2 and the water are absorbed into the absorption liquid. In some embodiments, a substantial portion of the product alcohol and the CO2 and at least a portion of the water are absorbed into the absorption liquid. In some embodiments, a substantial portion of the product alcohol and the water and at least a portion of the CO2 are absorbed into the absorption liquid. In some embodiments, the method further comprises prior to the (a) vaporizing step, one or both of (i) gas stripping a portion of the CO2 from the fermentation liquid feed and (ii) vaporizing a portion of the CO2 from the fermentation liquid feed. In some embodiments, a portion of the CO2 from the fermentation liquid feed is gas stripped from the fermentation liquid feed prior to the (a) vaporizing step, where the portion of the CO2 is gas stripped by countercurrent contact of the fermentation liquid feed with a noncondensible gas. In some embodiments, the method further comprises prior to the (a) vaporizing step, gas stripping a substantial portion of the CO2 and a portion of product alcohol from the fermentation liquid feed and vaporizing a portion of the CO2 from the fermentation liquid feed.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

FIGS. 7B and 7C illustrate Tables 8A and 8B, respectively, which summarize simulation model results of Example 7.

FIGS. 8B and 8C illustrate Tables 10A and 10B, respectively, which summarize simulation model results of Example 8.

FIGS. 9B and 9C illustrate Tables 12A and 12B, respectively, which summarize simulation model results of Example 9.

FIGS. 10B and 10C illustrate Tables 13A and 13B, respectively, which summarize simulation model results of Example 10.

DETAILED DESCRIPTION

Figure 1:
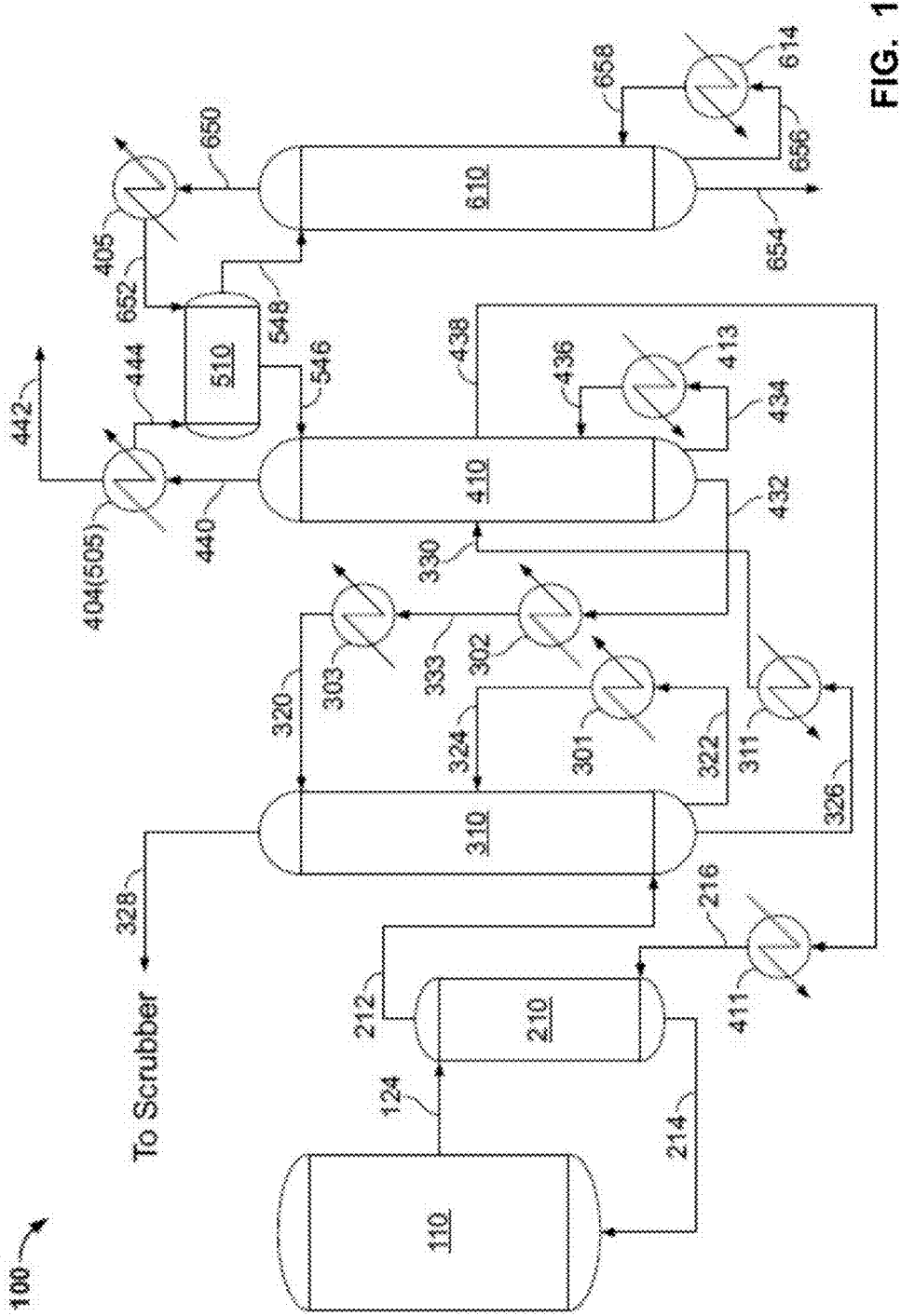
FIG. 1 illustrates an example system useful for practicing processes according to embodiments described herein.

The processes provided herein can be more fully understood from the following detailed description and accompanying figures which form a part of this application. Reference made to figures is intended to aid in the understanding of the processes described herein, and should not be construed as limiting. In addition, where process conditions are proposed in reference to a figure, these are supplied as an example and variation from these conditions is within the spirit of the invention.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

In order to further define this invention, the following terms and definitions are herein provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers may be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product comprising hydrolysable polysaccharides that provide fermentable sugars, including any sugars and starch derived from natural resources such as corn, sugar cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components, such as protein and/or lipids. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof. For example, mash or juice or molasses or hydrolysate may be formed from biomass by any processing known in the art for processing the biomass for purposes of fermentation, such as by milling, treating and/or liquefying and comprises fermentable sugar and may comprise an amount of water. For example, cellulosic and/or lignocellulosic biomass may be processed to obtain a hydrolysate containing fermentable sugars by any method known to one skilled in the art. Particularly useful is a low ammonia pretreatment as disclosed US Patent Application Publication US20070031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al., (Microbiol. Mol. Biol. Rev. 66:506-577, 2002).

The term "vacuum flash" or "flash" refers to a process step whereby a liquid stream from a fermentation vessel is passed to a separate vessel (which can be a multi-stage distillation column or a single-stage tank) which is held under vacuum. The reduction in pressure causes a fraction, typically no more than 10%, of the liquid stream to flash into the vapor phase. A liquid stream subjected to this step may be referred to as "flashed" or "partially vaporized" or "vaporized." In some embodiments where the "flash" is carried out in a multi-stage distillation column, the flash may also be referred to as a "distillation" or a "flash distillation."

The term "vacuum flash vessel" refers to the physical location in which at least a fraction of the liquid stream from the fermentation vessel flashes into the vapor phase.

The term "absorption liquid" as used herein refers to a liquid introduced into the process which is capable of absorbing any portion of the vapor phase produced during the flash.

The term "fermentation" as used herein refers to a process step whereby a carbon substrate is converted into a product, such as a product alcohol, by the action of microorganisms.

The term "fermentation broth" or "fermentation liquid" as used herein refers to the mixture of water, sugars, dissolved solids, suspended solids, microorganisms producing alcohol, product alcohol and all other constituents of the material held in the fermentation vessel in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentable carbon source" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; carbon substrates such as methane; and mixtures thereof. From time to time, as used herein the term "fermentable carbon source" can be used synonymously with "carbon substrate" or "fermentable carbon substrate." The carbon source includes carbon-derived from biomass.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstock include, but are not limited to, rye, wheat, barley, corn, corn mash, cane, cane mash, cellulosic material, lignocellulosic material, and mixtures thereof.

"Sugar" as used herein refers to oligosaccharides, disaccharides, and/or monosaccharides. The term "saccharide" also includes carbohydrates including starches, dextrans, glycogens, cellulose, pentosans, as well as sugars.

"Fermentable sugar" as used herein refers to one or more sugars capable of being metabolized by the microorganisms disclosed herein for the production of fermentative alcohol.

The term "product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers to the butanol isomers 1-butanol (1-BuOH), 2-butanol (2-BuOH), tert-butanol (t-BuOH), and/or isobutanol (iBuOH or i-BuOH or I-BUOH, also known as 2-methyl-1-propanol), either individually or as mixtures thereof.

The term "carboxylic acid" as used herein refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "recombinant microorganism" as used herein refers to a microorganism (e.g., bacteria, yeast) that has been engineered using molecular biological techniques. The microorganism can be optionally engineered to express a metabolic pathway, and/or the microorganism can be optionally engineered to reduce or eliminate undesired products and/or increase the efficiency of the desired metabolite. As an example, the recombinant microorganism may be engineered to express a biosynthetic pathway to produce an alcohol such as butanol.

"Substantial portion" as used herein with reference to a process stream or a component thereof, refers to at least about 50% of the indicated process stream or indicated component thereof. In some embodiments, a substantial portion may comprise at least about 60%, at least about 70%, at least about 80%, at least about 90%, or at least about 95% or the indicated process stream or indicated component thereof "Substantially" as used herein with reference to a process stream or a component thereof, refers to at least about 50% of the indicated process stream or indicated component thereof. In some embodiments, a substantial portion may comprise at least about 60%, at least about 70%, at least about 80%, at least about 90%, or at least about 95% or the indicated process stream or indicated component thereof.

"Any portion" as used herein with reference to a process stream refers to any fractional part of the stream which retains the composition of the stream, including the entire stream, as well as any component or components of the stream, including all components of the stream.

Provided herein are methods by which a fermentation liquid stream leaving a fermentation vessel is processed using a vacuum flash. The vacuum flash can be carried out in a flash tank (e.g., single-stage). Alternatively or in conjunction, the vacuum flash can be carried out in a distillation column (e.g., multi-stage) under conditions such that a flashed fermentation broth forms a vapor stream enriched in product alcohol and a bottoms stream substantially depleted in product alcohol are produced. As disclosed herein, the vapor stream from the flashed fermentation broth can be absorbed into a second liquid stream (e.g., absorption liquid) at a temperature that is higher than the temperature at which the vapor stream could be condensed on its own. Such processes are useful for fermentations which produce product alcohols (e.g., butanol) because of the desire to remove the product alcohol (e.g., butanol) during fermentation to diminish the impact on productivity and/or viability of the microorganisms in the fermentation. Processes are therefore provided which provide for effective product recovery during fermentation with minimized impact on the optimal fermentation conditions.

During a product alcohol fermentation, the product alcohol is produced in a fermentation liquid by a microorganism from a carbon substrate. In some embodiments, the carbon substrate is provided in a mash derived from a plant source. The fermentation can be carried out under conditions known to those of skill in the art to be appropriate for the microorganism. In some embodiments, the fermentation is carried out at temperatures of from about 25° C. to about 45° C. In some embodiments, the fermentation is carried out at temperatures of from about 28° C. to about 40° C. and in some embodiments, from about 30° C. to about 35° C. The fermentation liquid may comprise water and a product alcohol, and typically $CO_2$. To recover the product alcohol from the liquid using the methods provided herein, at least a portion of the fermentation liquid is removed from the fermentation vessel to a second vessel or "vaporization vessel" and is at least partially vaporized by vacuum flash. For example, in such embodiments, the vaporization can take place at temperatures of from about 25° C. to about 60° C. under vacuum. The vaporization can take place at pressures from about 0.3 to about 3 psia (about 20 mbar to about 200 mbar). It will be appreciated that the pressure can be about 0.3, about 0.4, about 0.5, about 1, about 2, or about 3 psia or less than about 3 psia. In some embodiments, the vaporization can take place at pressures of from about 0.5 to about 2 psia. In some embodiments, the vaporization can take place at a pressure of less than about 3 psia, or less than about 2 psia. Alternatively, the vacuum flash can be carried out in a multi-stage distillation column as described elsewhere herein under conditions described herein.

In one embodiment, the vaporization may be initiated and carried out during the fermentation process such that product alcohol is removed at about the same rate at which it is produced. It will be appreciated that the vaporization may be carried out at a rate and under conditions such that the product alcohol in the fermentation vessel is maintained below a preselected threshold. The preselected threshold may depend on the tolerance of the microorganism to the product. In some embodiments, the threshold is less than about 20 g/L (grams of product alcohol/liters of fermentation broth). In some embodiments, the threshold is less than about 5 g/L, less about 10 g/L, less than about 15 g/L, less than about 25 g/L, less than about 30 g/L, or less than about 40 g/L.

In some embodiments, the microorganism may be bacteria, cyanobacteria, filamentous fungi, or yeasts. In some embodiments, the bacteria may be selected from the group consisting of *Clostridium, Zymomonas, Escherichia, Salmonella, Serratia, Erwinia, Shigella, Rhodococcus, Pseudomonas, Bacillus, Lactobacillus, Enterococcus, Pediococcus, Alcaligenes, Klebsiella, Paenibacillus, Arthrobacter, Corynebacterium*, and *Brevibacterium*. In some embodiments, yeast may be selected from the group consisting of *Pichia, Yarrowia, Candida, Hansenula, Kluyveromyces, Issatchenkia, Schizosaccharomyces*, and *Saccharomyces*. In one embodiment, recombinant microorganisms may be selected from the group consisting of *Escherichia coli, Lactobacillus plantarum, Kluyveromyces lactis, Kluyveromyces marxianus*, and *Saccharomyces cerevisiae*. In one embodiment, the recombinant microorganism is yeast. In one embodiment, the recombinant microorganism is crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*.

Further, microorganisms, such as recombinant microorganisms, modified to have certain characteristics to benefit the production and recovery of a product alcohol are contemplated herein. For example, a microorganism with a certain level of thermotolerance such that elevated fermentation or feed stream temperatures may be more tolerated and therefore provide overall process efficiency. Further, where a fermentative microorganism performs advantageously under certain conditions characteristically, the processes described herein can be utilized to capitalize on such efficiencies. For example, a gas stripper may be used to provide effective air stripping and to provide oxygen for microaerobic microorganisms in the fermentation vessel.

Processes described herein can be used in conjunction with a number of product alcohols. Such alcohols include, but are not limited to, lower alkane alcohols such as butanol. In some embodiments, the processes described herein involve production of butanol by a recombinant microorganism capable of converting a carbon substrate to butanol. Microorganisms capable of converting a carbon substrate to butanol are known in the art and include, but are not limited to, recombinant microorganisms such as those described in U.S. Patent Application Publication Nos. 2007/0092957, 2007/0259410, 2008/0182308, 2009/0305363, and 2009/0305370; in U.S. Provisional Application Nos. 61/379,546 and 61/380,563; and in U.S. patent application Ser. No. 12/893,089.

In some embodiments of the methods described herein, the fermentation broth of a product alcohol-producing fermentation may be partially vaporized at temperatures from about 25° C. to about 60° C. and under vacuum conditions (e.g., about 0.3 psia to about 3.0 psia, about 20 mbar to about 200 mbar) to produce a vapor stream that comprises water, product alcohol (e.g., butanol), and $CO_2$, and this vapor stream may be contacted with an absorption liquid in an absorption device under similar temperature and vacuum conditions. In some embodiments, the absorption temperature may be higher than the vaporization temperature. For example, the absorption temperature can be about 5° C., about 10° C., about 15° C., about 20° C., about 25° C., about 30° C., or about 35° C. higher than the vaporization temperature. In some embodiments, the absorption pressure may be higher than the vaporization pressure. For example, the absorption pressure can be about 1 psia, about 2 psia, about 3 psia, about 4 psia, about 5 psia, about 10 psia, or about 15 psia (about 65 mbar to about 1 bar) higher than the vaporization pressure.

The absorption liquid preferably absorbs a portion of the product alcohol (e.g., butanol) out of the vapor stream. The absorption liquid minimizes the need for a reduction in temperature (e.g., chilling) and reduces the portion of the vapor stream that would require an increase in pressure (e.g., recompression). The absorption liquid may be tailored to optimize the removal of certain components of the vapor stream. For example, an absorption liquid comprising 2-ethyl hexanol and a glycol can be used to recover substantial portions of product alcohol (e.g., butanol) and water from the vapor stream. Furthermore, the heat from this absorption may provide at least a portion of the heat of vaporization.

In contrast to processes used in the art to treat gas streams that contain acid gasses such as $CO_2$ and $H_2S$ by absorption into specially designed absorption media (Gas Purification, 5th Edition, Arthur Kohl and Richard Neilsen 1997), the methods provided herein absorb any or all components of the vapor stream into an absorption liquid. Also, in contrast to processes used in the art to treat gas streams, the contact with the absorption liquid takes place at a sub-atmospheric pressure close to that of operation of the flash, and in some embodiments, substantially all of the vapor stream is absorbed. The flash and absorption units can be coupled in such a way as to minimize pressure drop between the two operations.

To recover the product alcohol, the heat of absorption is removed from the absorption liquid, for example, by circulation over a cooler. In such an embodiment, the heat can be removed from the circulating fluid using a cheaper cooling medium (e.g., using the fermentation liquid) than would be required for condensation of the vapor stream without an absorption liquid, the cheaper cooling typically being via an air cooler or a heat exchanger operating from a cooling water circuit or using, for example, river water directly. The amount of absorption liquid that would need to be re-circulated depends on the temperature rise that can be allowed over the absorption device, which can be an absorber, absorption column (e.g., multi-stage absorption column), spray tower, ejector-venturi scrubber, an agitated tank, a liquid ring vacuum pump, an eductor, or any such device or apparatus that enables the contacting of a vapor and a liquid. As an example, in a multi-stage absorption column, the upper temperature is limited by vapor pressures from the solution at the pressure of absorption while the lower temperature is limited by approach to the cold utility temperature (e.g., cooling water).

For processes provided herein, contact of the vapor stream with an absorption liquid is carried out under a vacuum, and can be carried out at pressures of from about 0.3 psia to about 3 psia (about 20 mbar to 200 mbar). In some embodiments, the contacting can take place at a pressure of less than about 3 psia, or less than about 2 psia. The contacting can be carried out at temperatures of from about 25° C. to about 60° C. In some embodiments, the vaporization step and the contacting step are carried out at the same pressure.

Suitable absorption liquids include those that comprise an organic molecule. In some embodiments, the organic molecule has a boiling point at least 30° C. greater than the boiling point of water. In some embodiments, the absorption liquid may comprise an organic molecule that exhibits a superior absorption affinity for butanol over water. In some embodiments, the organic molecule is an amine. In some embodiments, the amine is monoethanolamine (MEA), 2-amino 2-methyl propanol (AMP), methyldiethanolamine (MDEA), or a mixture thereof. In some embodiments, the molar ratio of absorption liquid amine to $CO_2$ in the vapor stream is at least about 1.01 to about 2, that is, the molar ratio is greater than about 1.

In some embodiments, the absorption liquid comprises potassium carbonate and ethylene glycol. In some embodiments, the absorption liquid comprises ethylene glycol. In some embodiments, the absorption liquid comprises MEA, AMP, MDEA, and any mixture thereof. In some embodiments, the absorption liquid comprises ethylene glycol and an amine such as MEA, AMP, MDEA, and a mixture thereof. In some embodiments, the absorption liquid comprises 2-ethyl hexanol (2-EH), isolauryl alcohol, phenol, and a mixture thereof. In some embodiments, the absorption liquid comprises a fatty acid, fatty ester, fatty alcohol, and mixtures thereof. The fatty acid, fatty ester, or fatty alcohol may be derived from corn oil, soybean oil, or castor oil.

The absorption liquid may comprise an ionic solution. In some embodiments, the ionic solution comprises a carbonate. In some embodiments, the carbonate is potassium carbonate because of its higher solubility compared to other common alkali metal carbonates. In some embodiments, the amount of carbonate (e.g., potassium carbonate) in the ionic solution is an amount sufficient for achieving absorption of at least a portion (or in embodiments, a substantial portion) of $CO_2$ from the vapor stream. In some embodiments, the molar ratio of carbonate (e.g., potassium carbonate) to $CO_2$ in the vapor stream is greater than about 1.

In some embodiments, the absorption liquid is an ionic liquid. Suitable absorption liquids for absorption of both water and product alcohol (e.g., butanol) include those with the following characteristics: 1) miscible with water and product alcohol (e.g., butanol); 2) normal boiling point of 130° C. or more, or of 150° C. or more; 3) thermal stability at the boiling point; 4) absence of precipitants when exposed to carbon dioxide at a ratio less than 5% weight/weight, or 10% weight/weight; and 5) low corrosivity.

In some embodiments, the methods provided herein use MEA as the absorption liquid. MEA solutions absorb water at a higher temperature than water would condense without the presence of the MEA solution. Additionally, butanol is soluble in the MEA solution and the MEA solution is also capable of absorbing $CO_2$.

In some embodiments, the methods provided herein use MDEA as the absorption liquid. MDEA solutions absorb water at a higher temperature than water would condense without the presence of the MDEA solution. Additionally, butanol is soluble in the MDEA solution and the MDEA solution is also capable of absorbing $CO_2$. While other amines could be used, MDEA also has the advantage that it does not form a carbamide and is therefore readily regenerated.

Suitable absorption liquids include, but are not limited to, organic liquids, high-boiling organic amines, and ionic liquids, as well as biologically-derived liquids of the above, or mixtures thereof.

Organic Liquids. Suitable organic liquids contain components which are soluble in water and water is soluble in the organic component. These liquids have a higher boiling point than water to facilitate absorption of water at a higher temperature than the condensation point of water. Typically these molecules will require at least two functional groups on their carbon backbones such as glycols and diacids. As examples, the absorption liquid can include ethylene glycol, ethylene glycol monomethyl ether, diethylene glycol, propylene glycol, dipropylene glycol, polyethylene glycols, polyethylene glycol ethers, polypropylene glycol ethers, or a mixture thereof. Biologically-derived 1,3-propanediol may also be used and may provide overall carbon-footprint benefit (see e.g., U.S. Pat. No. 7,759,393).

As water is readily soluble in, for example, ethylene glycol, organic liquids provide for absorption from the vapor phase. Further, the solubility of butanol in these liquids (in particular, ethylene glycol) is better than in water. In some embodiments, the organic liquid may also form an ionic solution. An example is potassium carbonate in ethylene glycol solution.

High-boiling Organic Amines. High boiling organic amines, such as alkanolamines, are suitable for use with the processes described herein. Like ethylene glycol, alkanolamines such as MEA and MDEA are miscible with water and facilitate absorption of water at a high temperature. They are also more miscible with butanol than butanol is with water. In addition, they absorb $CO_2$ absorption through a heat-reversible reaction.

In some embodiments, the absorption liquid includes a polyethylenimine or related polymeric amino system.

By way of non-limitative example, amines that can serve as absorption liquids for use with the processes described herein can include aliphatic or cycloaliphatic amines having from 4 to 12 carbons, alkanolamines having from 4 to 12 carbons, cyclic amines where 1 or 2 nitrogens together with 1 or 2 alkanediyl groups form 5-, 6-, or 7-membered rings, mixtures of the above solutions, and aqueous solutions of the above mixtures and solutions.

For example, the absorption liquid can include monoethanolamine (MEA), methylaminopropylamine (MAPA), piperazine, diethanolamine (DEA), triethanolamine (TEA), diethylethanolamine (DEEA), diisopropylamine (DIPA), aminoethoxyethanol (AEE), dimethylaminopropanol (DIMAP), and methyldiethanolamine (MDEA), any mixture thereof, or any aqueous solutions thereof.

Ionic Liquids. Ionic liquids are solutions comprising a cation and/or an anion, such as a variety of salts that are in solution at a temperature below 100° C. Examples of suitable ionic liquids include those described in U.S. Patent Application Publication Nos. 2010/0143993, 2010/0143994, and 2010/0143995, incorporated herein by reference. The presence of inorganic salts causes a reduction in the vapor pressure of water in the solution both by dilution and the increased ionization of water. Water-soluble salts are suitable for this process. Suitable for embodiments wherein water is absorbed are solutions comprising salts that are highly soluble in water, such as lithium bromide. Generally, the monovalent alkali metals, such as lithium, sodium, potassium will be chosen over other metals because of an increased solubility. The correct choice of anion can allow $CO_2$ to also be recovered in the process. Carbonate ion can be employed to absorb $CO_2$ in the aqueous phase by formation of the bicarbonate ion. Processes using potassium carbonate solutions are generally referred to as the Benfield Process which, prior to the disclosure herein, has not been used in conjunction with alcohol production fermentations to provide a temperature advantage for recovery of a fermentation product alcohol. In some embodiments, a mixed salt solution such as potassium carbonate and a potassium halide salt can be employed. While not wishing to be bound by theory, it is believed that such a mixed salt solution will increase the ionic strength of the solution to improve capture of water without causing precipitation of salts. It is noted that ionic liquids may absorb ethanol water and/or $CO_2$ from the vapor phase more efficiently than higher alcohols such as butanol (i.e., a C3 or higher product alcohol) as well as it can absorb ethanol.

Additional Absorption Liquids. Other examples of absorption liquids include 2-ethyl hexanol (2-EH), isolauryl alcohol, isocetyl alcohol, oleyl alcohol, phenol, fatty acids, fatty esters, fatty alcohols, and mixtures thereof. The fatty acids, fatty esters, and fatty alcohols may be derived from corn oil, soybean oil, or castor oil.

Additional examples of absorption liquids include, but are not limited to, acids, alcohols, amides, esters, ketones, carbonates, phosphates, salt solutions such as brine, and mixtures thereof.

The absorption fluid may comprise one or more carboxylic acids. As an example, the carboxylic acid may react with the product alcohol (e.g., butanol) in the presence of a catalyst to form an ester which is subsequently hydrolyzed to recover the product alcohol and regenerate the carboxylic acid (i.e., absorption liquid) (see, e.g., U.S. patent application Ser. No. 13/162,868 and U.S. patent application Ser. No. 13/193,147; the entire disclosures of which are incorporated in their entirety herein by reference). In some embodiments, the ester may be hydrolyzed in the presence of a hydrolysis catalyst such as an acid catalyst, base, an organic acid, an inorganic acid, a water soluble acid, or water insoluble acid. In some embodiments, the hydrolysis catalyst comprises an enzyme capable of hydrolyzing the ester to form a carboxylic acid and product alcohol (e.g., butanol). In some embodiments, the enzyme is an esterase, lipase, phospholipase, or lysophospholipase.

The temperature at the onset of the absorption of the vapor stream into the absorption liquid is greater than the temperature at the onset of condensation of the vapor stream in the absence of the absorption liquid. The temperature of onset of absorption or condensation can be assessed by calculation using standard vapor liquid equilibrium methods that are based on experimental data or by direct measurement from the process. In some embodiments, the temperature at the onset of the absorption of the vapor stream into the absorption liquid phase is greater than the temperature at the onset of condensation of the vapor stream in the absence of the absorption liquid by at least about 2° C.; at least about 3° C.; at least about 5° C.; at least about 10° C.; at least about 15° C.; at least about 20° C.; and at least about 30° C. Equipped with this disclosure, one of skill in the art will be readily able to use the processes described herein to minimize the cost of cooling plus the cost of regenerating the solvent.

As discussed above, the fermentation broth is partially vaporized at temperatures from about 25° C. to about 60° C. and under vacuum conditions (e.g., about 0.3 to about 3.0 psia; about 20 mbar to about 200 mbar) to produce a vapor stream that comprises water, product alcohol (e.g., butanol), and $CO_2$, and this vapor stream is contacted with an absorption liquid in an absorption device under similar temperature and vacuum conditions. In another embodiment, the absorption temperature is higher than the vaporization temperature. For example, the absorption temperature can be about 5° C., about 10° C., about 15° C., about 20° C., about 25° C., about 30° C., about 35° C. higher than the vaporization temperature. In some embodiments, the absorption pressure is higher than the vaporization pressure. For example, the absorption pressure can be about 1 psia, about 2 psia, about 3 psia, about 4 psia, about 5 psia, about 10 psia, or about 15 psia (about 65 mbar to about 1 bar) higher than the vaporization pressure.

It will be appreciated that it is beneficial to absorb as much of the vapor stream as possible into the absorption liquid. In some embodiments, at least about 50% of the vapor stream is captured by the absorption liquid. In some embodiments, at least about 60%, at least about 70%, at least about 80%, at least about 90%, or at least about 99% of the vapor stream is absorbed into the absorption liquid. In some embodiments, the vapor stream comprises about 50-80% by mass of water, about 10-40% by mass of butanol, and about 0-20% by mass $CO_2$. It will be appreciated that absorption, condensation, and similar processes are made easier by establishing a low concentration of carbon dioxide in the vapor stream. It will be further appreciated that absorption, condensation, and similar processes are made easier by establishing a high mass ratio of butanol to carbon dioxide. This ratio is on the order of 1 to 2 parts butanol to 100 parts carbon dioxide for the fermentation vessel vent. In some embodiments, this ratio is increased to 1 to 5 parts butanol to 1 part carbon dioxide. In some embodiments, this ratio is increased to 5 to 30 parts butanol to 1 part carbon dioxide. In some embodiments, this ratio is increased to 10 to 100 parts butanol to 1 part carbon dioxide.

It will be further appreciated that recovery of butanol will be made easier by condensation from a stream of a high ratio of butanol to water at pressures greater than 0.5 psig. In some embodiments, this pressure is increased to 1 to 30 psig.

In some embodiments, the absorption liquid absorbs a substantial portion of the $CO_2$ from the vapor stream. In some embodiments, at least about 50%, at least about 60%, at least about 70%, at least about 80%, at least about 90%, at least about 95%, or at least about 99% of the $CO_2$ is absorbed. For such embodiments, the absorption liquid can be MEA MEA, MDEA, AMP, or ethylene glycol mixed with one or more of MEA, MDEA, AMP and potassium carbonate.

Thus, provided herein is a process comprising: partially vaporizing a fermentation liquid comprising water and a product alcohol and optionally $CO_2$ wherein a fermentation vapor stream is produced; and contacting the fermentation vapor stream with an absorption liquid phase wherein any portion of the vapor stream is absorbed into the absorption liquid phase.

In some embodiments where product alcohol is absorbed into the absorption liquid, the product alcohol can be recovered from the absorption liquid such that the absorption liquid is concurrently regenerated and recycled. The recovery and regeneration can be achieved using a process comprising: pumping an absorption liquid to a higher pressure than the pressure at which vaporization and absorption took place, such as at a pressure at or above atmospheric pressure, which would allow venting of residual $CO_2$ from the process; feeding the absorption liquid to a distillation column comprising a stripping section and optionally a rectification section; distilling the absorption liquid such that a bottoms liquid product and a tops vapor product are produced; and recovering the bottoms product comprising water and the absorption liquid from the distillation column. The feed to the distillation column can be preheated to reduce the energy input required at the base of the distillation column using techniques well known to those skilled in the art.

The components removed from the absorption liquid phase and recovered in the tops vapor product from the distillation can be further separated using conventional methods such as condensation, distillation, and decantation, or a combination thereof. Depending on the composition of the fermentation vapor stream and the absorption liquid employed, in some embodiments, the absorption liquid, post vapor stream contact, will contain a combination of water, product alcohol and optionally, $CO_2$, and in certain embodiments, all three components.

FIG. 1 depicts an exemplary configuration of equipment, heat exchangers, and product streams for an embodiment of a process 100 described herein. A fermentation to produce butanol (or other product alcohol(s)) is performed in a fermentation vessel 110, and the concentration of butanol in fermentation vessel 110 approaches the tolerance level of the microorganism. Fermentation liquid is purged from fermentation vessel 110 via a stream 124 to a vacuum flash vessel 210 to facilitate the removal of butanol. In some embodiments, vacuum flash vessel 210 is a flash tank, and the pressure in vessel 210 is maintained at such a pressure that in combination with heat that is supplied in the form of partially vaporized water in a stream 216, a sufficient purge of butanol is achieved in a vapor stream 212 so as to permit butanol levels in vessel 110 to be maintained below a preselected threshold given that the remaining liquid from vacuum flash vessel 210 is returned to fermentation vessel 110 via a stream 214.

The pressure in vessel 210 can be sufficiently low to achieve the cooling necessary to keep remaining liquid stream 214 and vessel 110 at a temperature acceptable to maintain productivity of the microorganism. The operating pressure of vessel 210 can be between about 0.3 to about 3 psia (about 20 mbar to about 200 mbar). It will be appreciated that the pressure can be about 0.3 psia, about 0.4 psia, about 0.5 psia, about 1 psia, about 2 psia, or about 3 psia. In some embodiments, the ratio of the concentration of butanol in stream 214 to the concentration of butanol in stream 124 is about 0.9 to about 0.5. It will be appreciated that the ratio can be about 0.9, about 0.8, about 0.7, about 0.6, or about 0.5. Vapor stream 212 comprises water, butanol, and $CO_2$. Stream 212 enters an absorption column 310 where it is contacted with absorption liquid streams 320 and 324. Absorption liquid streams 320 and 324 comprise an absorption liquid.

In a non-limiting example, the absorption liquid is an amine such as MDEA. In a non-limiting example, the absorption liquid is potassium carbonate in ethylene glycol. The temperature and absorbent concentrations of 320 and 324 are maintained at such a level that vapor stream 212 is substantially absorbed. In some embodiments, vapor stream 212 is substantially absorbed at a temperature of more than about 36° C. while the dew point of stream 212 is less than about 30° C. Residual vapor is removed via a vacuum system via stream 328 and will exit to a plant scrubbing system. There is a liquid recycle stream 322 drawn from the bottom of column 310 and cooled in a cooler 301 to produce a stream 324 which is circulated back to column 310. In some embodiments, a flow rate of stream 322 will be selected such that the temperature rise between streams 324 and 322 will be about 3° C. to about 8° C. A liquid purge is taken from column 310 via a stream 326 which includes $CO_2$, butanol, and water absorbed from vapor stream 212 and the absorption liquid. Stream 326 is pumped (pump not shown) to raise its pressure to approximately atmospheric or higher, and is optionally heated in a heater 311 to produce a stream 330. Heater 311 can conveniently be heat integrated with a cooler 302 as discussed below.

Stream 330 enters a stripping column 410 which comprises a stripping section and a rectification section using contacting devices (e.g., trays or packing) known to those of skilled in the art. In the stripping section, $CO_2$, butanol, and a substantial fraction of the water is stripped from the absorption liquid of stream 330. In some embodiments, the pressure in stripping column 410 is approximately atmospheric and the bottom of stripping column 410 is heated to a temperature sufficient to assure that substantially all of the butanol is stripped and the water content of a liquid phase stream 432 including regenerated absorption liquid does not change over time. In some embodiments, the water concentration of liquid phase 432 exiting the bottom of column 410 is 10%-40% by mass. Material is circulated from the bottom of column 410 via a stream 434. Stream 434 passes to a heater 413 to produce a stream 436 which is returned to vessel 410. In some embodiments, the configuration of heater 413 can be of a kettle or thermosyphon readily designed by a person skilled in the art.

Regenerated absorption liquid is pumped (pump not shown) from the bottom of vessel 410 via stream 432, which can first be optionally cooled prior to introduction to absorption column 310. As shown in FIG. 1, in some embodiments, regenerated absorption liquid stream 432 is cooled in cooler 302 to produce a stream 333. As mentioned above, cooler 302 can conveniently be heat integrated with heater 311 for cooling stream 432. Stream 333 can then optionally be further cooled via cooler 303 to produce cool absorption liquid stream 320. In some embodiments, a side stream purge is taken from the rectification section of stripping column 410 via a stream 438. Stream 438 can be substantially free of absorption liquid and $CO_2$ and can contain about 1-3% butanol with the remainder being water. The water that is contained in stream 330 is substantially removed, via streams 438 and 432, from the downstream part of the process which includes column 410 and later-described decanter vessel 510 and butanol column 610. Control of stream 438 is such as to achieve the desired water level in stream 432. Stream 438 passes to a heater 411 and will be partially vaporized to form stream 216 which is fed to flash vessel 210. As described above, heat from stream 216 can help achieve the balance between vessel 210 and vessel 110 so as to effect a sufficient purge of butanol from fermentation liquid feed 124 via vapor stream 212 so as to permit butanol levels in vessel 110 to be maintained below a preselected threshold. In some embodiments, heater 411 can conveniently be heat integrated with cooler 404.

Vapor leaves the top of stripping column 410 via a stream 440 and passes to a cooler 404 and separator 505 by which stream 440 is substantially condensed and separated from a residual vapor stream 442 to produce a liquid stream 444. Stream 440 can be substantially free of absorption liquid because of the action of the rectification section in stripping column 410. Residual vapor stream 442 passes to a plant scrubbing system (not shown). Stream 442 includes a major part of the $CO_2$ fed to stripping column 410, while a major part of the water and butanol of stream 440 is condensed to form stream 444. Cooler 404 can be conveniently heat integrated with heater 411 and a heater 614 (further discussed below).

Liquid stream 444 passes to a decanter vessel 510, which also receives a stream 652 discussed below. Material in decanter vessel 510 will split into an aqueous liquid phase 546 and an organic liquid phase 548. In some embodiments, the aqueous phase or a portion thereof can be returned to the top of the rectification section of vessel 410 via stream 546. In some embodiments, a portion of either or both of stream 546 and stream 438 (discussed above) can be directed to a beer column (not shown).

The organic phase from decanter vessel 510 leaves via stream 548 and passes to a butanol column 610, which comprises at least a stripping section. Heat is provided to operate column 610 via a re-circulating loop of a stream 656 through heater 614 to produce a stream 658, which is returned to column 610. In some embodiments, the configuration of heater 614 can be of a kettle or thermosyphon readily designed by a person skilled in the art. If the operating pressure of column 610 is sufficiently below that of column 410 and cooler 404, then heater 614 can be conveniently heat integrated with cooler 404. The butanol product is taken from the bottom of column 610 via a stream 654. A vapor overhead stream 650 from column 610 passes to a cooler 405 and is condensed to produce stream 652. Stream 652 is pumped to decanter vessel 510 (pump not shown) where it can be split into aqueous and organic liquid phases.

In some embodiments, vacuum flash vessel 210 for achieving vaporization of fermentation liquid stream 124 is a multi-stage distillation column 210, instead of a flash tank as described above (which has only one stage). In such embodiments, fermentation liquid feed 124 containing product alcohol is supplied from fermentation vessel 110 at a flow rate to multi-stage distillation column 210. Fermentation liquid feed 124 is then partially vaporized in multi-stage distillation column 210 to produce vapor stream 212 enriched in product alcohol and bottoms stream 214 depleted in product alcohol. In contrast to vaporization carried out in a flash tank as described above, the distillation column can be operated such that the vapor is subjected to more than one stage. The multi-stage distillation column can have any number of stages, for example, from 2 to 8 or more. In some embodiments, the distillation column is a 6-stage column. As one of skill in the art will appreciate, this leads to a reduced concentration of product alcohol in bottoms stream 214 (which, in some embodiments, is returned to fermentation vessel 110, as shown in FIG. 1). Because product alcohol can be removed from fermentation vessel 110 more efficiently using distillation column 210 for the vaporization, the flow rate to the distillation column can be lower than the flow rate to a single-stage vacuum flash tank and still provide for sufficient removal of product alcohol from fermentation vessel 110. A lower flow rate from fermentation vessel 110 allows for venting of a greater fraction of $CO_2$ from the fermentation vessel, thereby lowering the flow rate of carbon dioxide vented from vessel 210 by about 2 to about 5 times or more and therefore, provides for reduced $CO_2$ in streams subjected to further processing. Similarly, in some embodiments wherein alcohol-depleted bottoms stream 214 or a portion thereof is returned to fermentation vessel 110, more efficient removal of product alcohol from fermentation liquid feed stream 124 allows for decreased flow rate to multi-stage distillation column 210 and likewise allows for a decrease in the flow rate of bottoms stream 214 back to the fermentation vessel. In this configuration, it is possible to return a bottoms stream of higher temperature to the fermentation vessel without disturbing the temperature of the fermentation beyond acceptable ranges, therefore allowing for the multi-stage distillation column to be operated at higher temperature than would otherwise be considered acceptable for a conventional single-stage vacuum flash tank.

Multi-stage distillation column 210 can be a conventional vacuum distillation column known to those of skill in the art. To achieve the advantages mentioned above, the multi-stage distillation column is operated such that the ratio of concentration of product alcohol in bottoms stream 214 is no more than about 90% of the concentration of feed 124, no more than about 50% of the concentration in feed 124, no more than about 10% of the concentration in feed 124, or in some embodiments, no more than about 1% of the concentration in feed 124. In some embodiments, multi-stage distillation column 210 is operated at a temperature range of from about 10° C. to about 65° C. and in a pressure range of from about 0.2 psia to any pressure below atmospheric pressure. In some embodiments, multi-stage distillation column 210 is operated at a temperature range of from about 25° C. to about 60° C. and in a pressure range of from about 0.3 to about 3 psia (about 20 mbar to about 200 mbar). In some embodiments, the bottom temperature is about 46° C. and the top temperature is about 36° C.

As with the conventional vacuum flash tank described above, the flow rate to the multi-stage distillation column and the operation thereof are selected such that the titer of product alcohol in fermentation vessel 110 is maintained below a predetermined threshold level selected in consideration of the tolerance of the microorganism to the product alcohol. Consequently, in some embodiments where bottoms stream 214 or a portion thereof is returned to fermentation vessel 110, it is advantageous to maintain a low concentration of product alcohol in the return stream. In some embodiments, bottoms stream 214 contains less than about 10 g/L, less than about 7 g/L, less than about 5 g/L, less than about 2.5 g/L, or less than about 1 g/L of the product alcohol.

In some embodiments, the presence of carbon dioxide in the fermentation liquid feed to vacuum flash vessel 210 (which can be a vacuum flash tank or a distillation column, as discussed above) can affect subsequent recovery of the product alcohol, for example, recovery by condensation. To reduce or substantially eliminate the amount of carbon dioxide present in the fermentation liquid feed to vessel 210, in embodiments presented herein, carbon dioxide can be pre-flashed from the fermentation liquid at a pressure intermediate between atmospheric pressure and the pressure of the flash at vessel 210. For example, in any of the processes described herein, fermentation liquid could be fed to a tank that is maintained at a partial vacuum which is sufficient to pre-flash at least a portion of the carbon dioxide from the feed into a resultant vapor but not sufficient to cause the water and alcohol to boil. For example, pre-flashing at about 3 psia to about 12 psia may result in a vapor that can be further treated. Such treatment can include compression and in some embodiments, cooling of the resultant vapor including the carbon dioxide (and any associated water and alcohol also present) prior to discharge to the atmosphere. In other embodiments, carbon dioxide can be partially stripped from the fermentation liquid with a noncondensible gas such as air or nitrogen. For example, fermentation liquid can be counter-currently contacted with a noncondensible gas in a single-stage or multi-stage vapor liquid contactor (e.g., a stripping column or a degassing cyclone) operating near atmospheric pressure. As an example, a three stage countercurrent column could be used which accepts sterile compressed air at the bottom in a ratio of 0.2 to 5.0 mass units of air per mass units of carbon dioxide in the fermentation liquid, which is fed to the top of the column. The air-stripped carbon dioxide and some quantity of product alcohol and water can then be treated (e.g., scrubbed) to remove this alcohol before discharge to the atmosphere. In another embodiment, the fermentation liquid is pre-flashed at 3 to 12 psia and simultaneously stripped with a noncondensible gas. In another embodiment, the pre-flashing and the stripping can be carried out using a static mixer and a degassing cyclone. Such removal of an amount of carbon dioxide according to the embodiments described herein can reduce the complications that carbon dioxide can have on the downstream recovery of the alcohol vapor formed in vacuum flash vessel 210.

Figure 2:
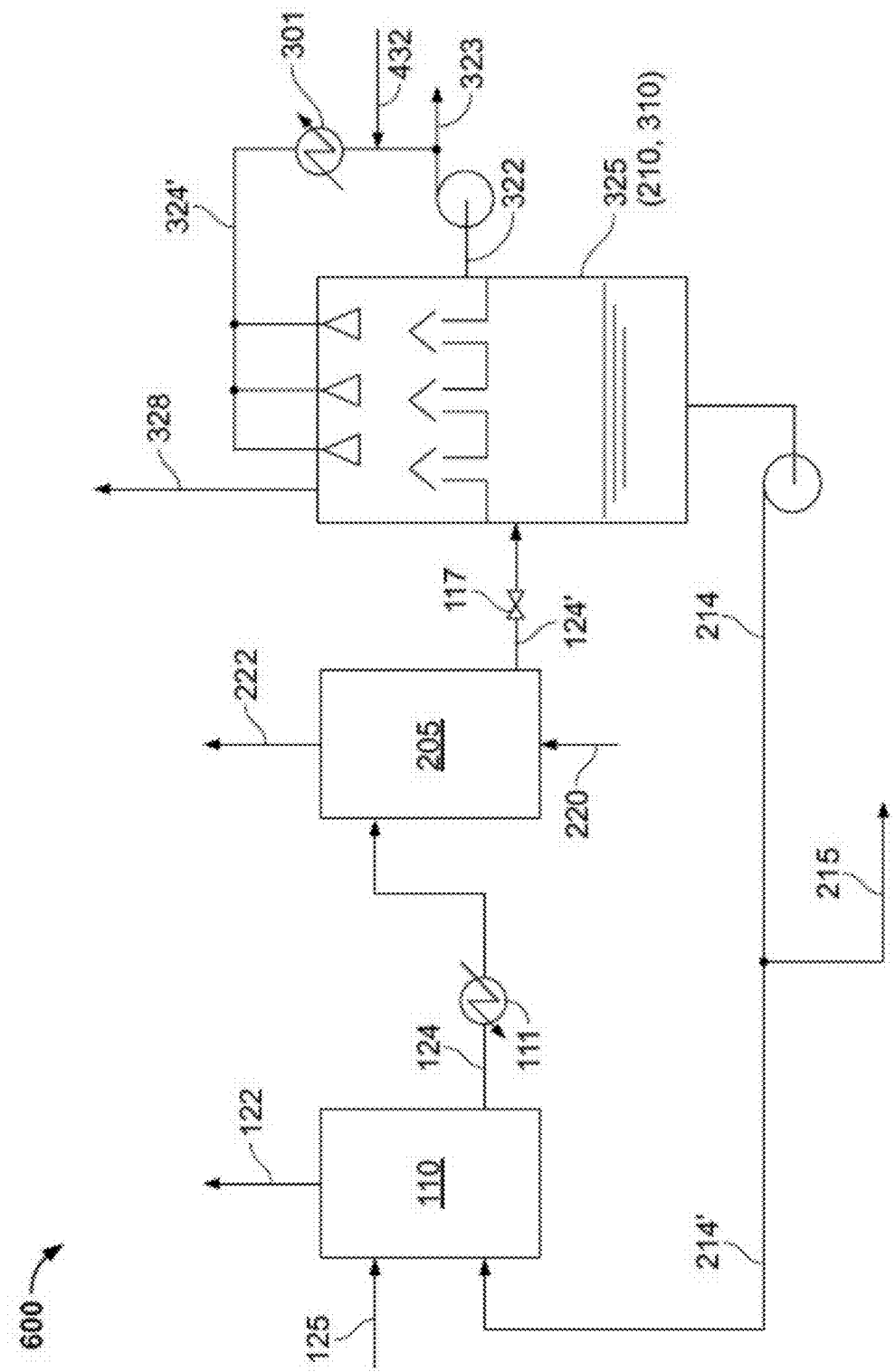
FIG. 2 illustrates an example system useful for practicing processes according to embodiments described herein.

FIG. 2 illustrates an exemplary process 600 in which at least a portion of carbon dioxide is gas stripped from the fermentation feed upstream of flash vessel 210. Referring to FIG. 2, a stream 125 of mash, yeast, and nutrients is introduced into fermentation vessel 110. A stream 122 including carbon dioxide is vented from fermentation vessel 110 to a water scrubber system (not shown). Stream 124 of fermentation liquid is heated in a heater 111 and introduced via a pump (not shown) into a multi-stage, countercurrent gas stripper 205. Stream 124 is contacted with a stream 220 of noncondensible gas, preferably an inert gas. In some embodiments, gas stream 220 is air or nitrogen. It should be apparent to one skilled in the art that by varying the number of stages in stripper 205 and the mass flow ratio of stripping gas 220 to fermentation liquid 124, it is possible to remove at least about 50% of the carbon dioxide in the fermentation liquid, at least about 55%, at least about 60%, at least about 65%, at least about 70%, at least about 75%, or at least about 80% of the carbon dioxide in the fermentation liquid. A stream 222 including stripping gas 220 and stripped carbon dioxide is vented from gas stripper 205. Stream 222 can be further treated, for example, by conveying stream 222 to a water scrubber system (not shown).

A stream 124' of carbon dioxide-depleted fermentation liquid is passed through a valve 117 into a multi-compartment vessel 325, which includes vacuum flash vessel 210 and absorption column 310. In the embodiment of FIG. 2, flash vessel 210 is a vacuum flash tank that is a compartment of multi-compartment vessel 325. Vapor, rich in product alcohol, generated in the flash tank passes into a second compartment of multi-compartment vessel 325 and is exposed to cool absorbent liquid stream 324' which causes substantial absorption of the vapor. Residual, unabsorbed vapor and inert gases are vented from multi-compartment vessel 325 via stream 328, which can then be conveyed through a compressor train (not shown in FIG. 2) in which vapor stream 328 is passed through compressors with intercoolers and exhausted through a water scrubber system. For example, this compressor train can be similar to that shown and described below in Example 9 with reference to FIG. 9A. Liquid recycle stream 322 of absorption liquid is drawn from multi-compartment vessel 325, circulated at high rate through cooler 301 to remove the heat of absorption, and returned to multi-compartment vessel 325 as part of cool absorbent liquid stream 324'. A stream 323 of rich absorbent is drawn from the circulation loop of recycle stream 322 and regenerated via a regeneration process. Regenerated absorption liquid is returned via stream 432 to the circulation loop, cooled through cooler 301, and returned to multi-compartment vessel 325 as part of cool absorbent liquid stream 324'. The regeneration process (not shown in FIG. 2) can be similar to that shown and described below in Example 8 with reference to FIG. 8A.

Fermentation liquid 214, partially depleted in alcohol, is pumped from the vacuum flash tank of multi-compartment vessel 325. A portion 215 of fermentation liquid 214 can be advanced to additional product alcohol recovery systems for recovery of product alcohol, water, and nonfermentables preferably when the fermentable sugars have been substantially depleted, and the remainder 214' of fermentation liquid 214 can be returned to fermentation vessel to further ferment the sugars therein for alcohol production.

It should be apparent to one skilled in the art that a vacuum column can be substituted for the vacuum flash tank of multi-compartment vessel 325 in the embodiment of FIG. 2, without departing from the scope of the present invention. Also, it should be apparent that flash vessel 210 and absorption column 310 can be separate vessels connected by conduits, similar to process 100 of FIG. 1, rather than being incorporated in multi-compartment vessel 325. Likewise, in some embodiments, any of the processes provided herein, including process 100 of FIG. 1, can be alternatively configured such that flash vessel 210 and absorption column 310 are incorporated in the same vessel such as the multi-compartment vessel 325 described above.

As an example of one embodiment of the methods of the invention, mash is added to a fermentation vessel that includes a pump which allows for the circulation of mash through an external heat exchanger. For example, mash is continually circulated out of the fermentation vessel to a water cooled heat exchanger and returned to the fermentation vessel in order to control the temperature of the of the mash. A constant circulation flow is maintained throughout the fermentation by the pump which may be designed, for example, to turn over the entire contents of mash in a filled fermentation over a specific time period (e.g., every 2 to 3 hours). Cooling water flow to the heat exchanger may be varied in order to maintain a desired mash temperature throughout the fermentation that is conducive to microorganism activity. This cooling water is optionally chilled when ambient conditions hinder cooling. When the temperature of the circulating mash is suitable, a volume of mash that has been used in a separate smaller vessel to activate and propagate the microorganism (e.g., yeast) may be transferred to the fermentation vessel. Mash feeding may be continued until a specified fermentation vessel capacity has been reached (e.g., 95% of the vessel capacity) over a certain period of time (e.g., 10-20 hours). In some embodiments, there may be one or more fermentation vessels (e.g., 1, 2, 3, 4, or more fermentation vessels). In one embodiment, the circulation loop for one fermentation vessel may be carried out for at least the time additional fermentation vessels (e.g., 1, 2, or 3 additional fermentation vessels) are filled. The additional fermentation vessels may be filled simultaneously or sequentially.

At a time point during fermentation, accumulation of product alcohol (e.g., butanol) may reach a level that negatively impacts the rate of further product alcohol production. The product alcohol may be transferred out of the fermentation broth in order to maintain a constant accumulation level of product alcohol that will allow the depletion of the remaining fermentable sugars in the fermentation broth. To achieve the removal of product alcohol, the circulation flow may be redirected through a path that reduces pressure of the fermentation broth via two stages of flashing. In a first-stage flash, the pressure may be reduced to a certain range (e.g., a range of about 3.0 psia to about 12.0 psia) using equipment, for example, that may include a flash tank, a degassing cyclone, air stripping column, or equivalent equipment and/or device that enables vapor liquid separation. A substantial portion of dissolved gases including carbon dioxide is released as a vapor in this first-stage flash. The fermentation broth continues from this first-stage flash device to a second-stage flash device where the pressure is further reduced (e.g., a range of about 0.3 psia-about 3.0 psia). A substantial portion of dissolved volatile components including carbon dioxide, water, and product alcohol (e.g., butanol) is released as a vapor in this second-stage flash. This mass transfer of volatile components from the liquid to vapor state also results in a concomitant transfer of heat out of the fermentation broth ("heat of vaporization"). Accordingly, this second-stage flash may be designed to simultaneously enable the transfer of heat and mass to accomplish vaporization. The fermentation broth from this second-stage flash may be pumped back to a pressure suitable for re-entering the fermentation vessel. The returned fermentation broth is at a temperature that is below the temperature inside the fermentation vessel and contains product alcohol (e.g., butanol) at a concentration that is below the product alcohol concentration inside the fermentation vessel such that the continual operation of this circulation path will enable a constant temperature and product alcohol concentration throughout the fermentation process.

Heat may be needed to transfer product alcohol out of the fermentation broth in the second-stage flash device. In one embodiment, the heat may be transferred to the fermentation broth indirectly through an exchanger upstream of the second-stage flash. In another embodiment, heat may be transferred indirectly to the fermentation broth during the second-stage flash or during vaporization. For example, both the transfer of heat and the vaporization of the fermentation broth may be accomplished using a device such as a falling film evaporator. In another embodiment, heat may be injected directly into the fermentation broth or into the second-stage flash via a carrier fluid. The carrier fluid may be a liquid or vapor stream comprising a portion of water at a temperature higher than the temperature inside the second-stage flash device. In some embodiments, the carrier fluid introduces no significant negative impact on the viability and productivity of the fermenting microorganism.

The vapor produced in the second-stage flash may comprise carbon dioxide, water, and product alcohol (e.g., butanol). The vapor may have a mass ratio of water to product alcohol (e.g., butanol) that ranges from 2 lbs water per lb product alcohol to more than 5 lbs water per lb of product alcohol depending on the concentration of product alcohol that is targeted in the fermentation broth. In one embodiment of the methods of the invention, the vapor may be immediately contacted with an absorption liquid such as a low volatility absorption liquid. The absorption liquid may be immiscible with water and may also exhibit a superior absorption affinity for product alcohol (e.g, butanol) over water. For example, the absorption liquid may comprise, but is not limited to, MEA, AMP, MDEA, glycols, potassium carbonate, 2-ethyl hexanol, isolauryl alcohol, isocetyl alcohol, oleyl alcohol, phenol, fatty acids, fatty esters, fatty alcohol and mixtures thereof.

Contacting the vapor with the absorption liquid may be effected, for example, in a absorption device such as, but not limited to, absorber, absorption column (e.g., multi-stage absorption column), spray tower, ejector-venturi scrubber, an agitated tank, a liquid ring vacuum pump, an eductor, or any such device or apparatus that enables the contacting of a vapor and a liquid. The contact of the vapor with the absorption liquid will form an absorption liquid phase and optionally, a residual vapor phase. For example, a portion of the vapor is absorbed to form an absorption liquid phase, and a portion of the vapor that is not absorbed forms a residual vapor phase.

In some embodiments, the absorption liquid phase comprises a substantial portion of the product alcohol and at least a portion of the $CO_2$ and water. In some embodiments, the absorption liquid phase comprises a substantial portion of the product alcohol and water and at least a portion of $CO_2$. In some embodiments, the absorption liquid phase comprises a substantial portion of product alcohol and $CO_2$ and at least a portion of water. In some embodiments, the absorption liquid phase comprises a substantial portion of product alcohol, water, and $CO_2$.

In one embodiment, an ejector-venturi scrubber may be utilized to bring the vapor into contact with the absorption liquid through a draft that is induced by the flow of the absorption liquid. Subsequently, the discharge of the ejector-venturi scrubber may be separated into a residual vapor phase and an absorption liquid phase in a flash tank.

In some embodiments, the product alcohol (e.g., butanol) of the vapor stream may be absorbed into the absorption liquid leading to a volume reduction of the vapor flowing through the absorption device. As the product alcohol is absorbed by the absorption liquid, the temperature of the absorption liquid will rise due to the heat of absorption. This temperature rise may be controlled by re-circulating the absorption liquid through the absorption device so as to dissipate the heat of absorption over a larger mass flow. For example, in embodiments where an ejector-venturi scrubber is used, a larger flow may also be favorable for creating more draft as described above. The amount of temperature rise may also be dependent on the pressure rise that is achieved by the absorption device. The absorption liquid phase may be discharged at a temperature in the range of 30° C. to 80° C. depending on the pressure at the discharge of the absorption device.

The heat of absorption may be returned to the second-stage flash to provide for the heat of vaporization. In one embodiment, the absorption liquid phase may be exchanged with fermentation broth upstream of the second-stage flash which results in a temporary rise in fermentation broth temperature immediately before the second-stage flash. In another embodiment, this absorption liquid phase may be heat exchanged during the second-stage flash to deliver heat to the vaporization process. In a further embodiment, a portion of the fermentation broth leaving the second-stage flash may be processed through a heat exchanger to remove heat from the absorption liquid phase and deliver the heat back to the second-stage flash via direct injection of the fermentation broth. Enough heat may be exchanged between the absorption liquid phase and the second-stage flash such that no additional cooling of the absorption liquid may be required at steady state.

Figure 11:
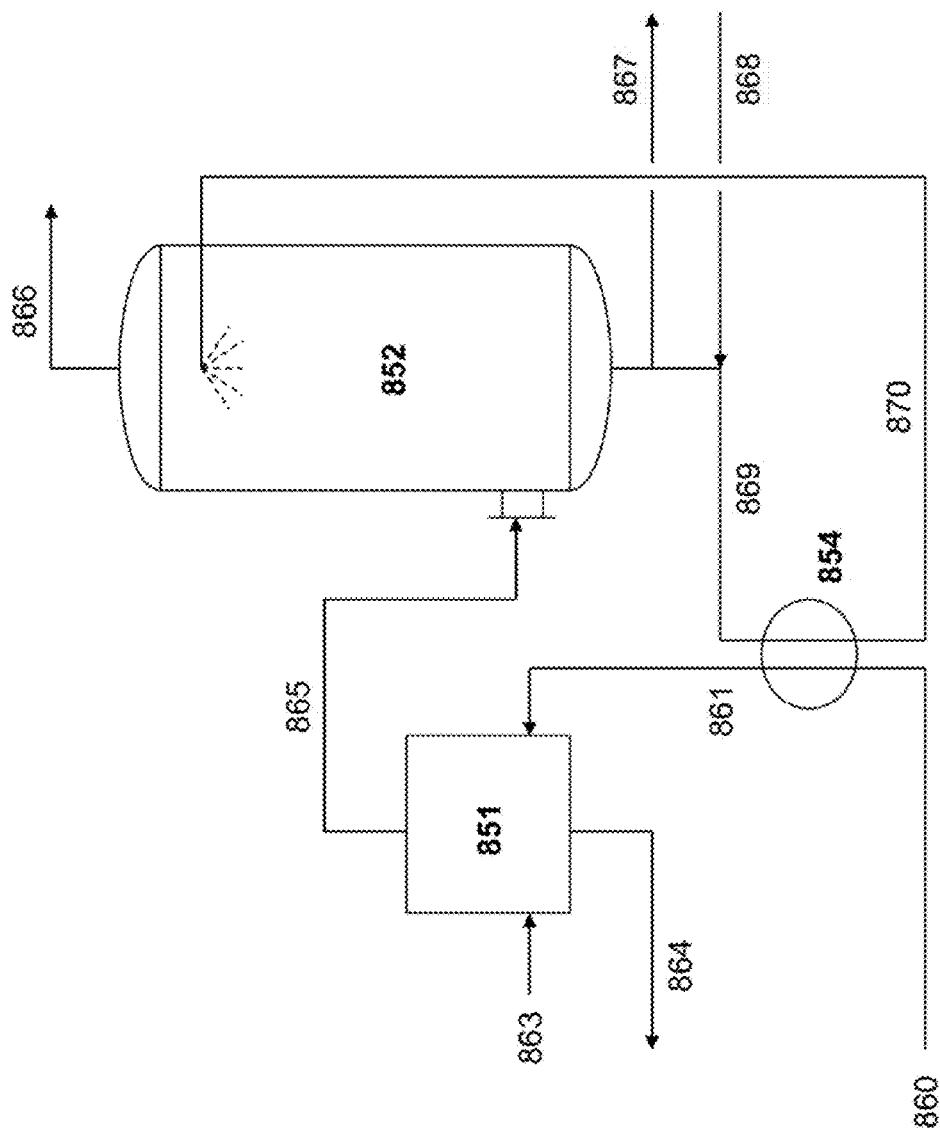
FIG. 11 illustrates an example system useful for practicing processes according to embodiments described herein.

FIG. 11 illustrates an exemplary process of the invention. Fermentation broth 860 from a fermentation vessel enters heat exchanger 854 where the fermentation broth 860 is heated by the absorption liquid phase 869. The heated fermentation broth 861 enters a low pressure flash 851 and vapor stream 865 is formed. The fermentation broth 864 exits the bottom of flash 851 with a concentration of product alcohol that is less than the concentration of product alcohol in fermentation broth 861. Furthermore, the temperature of fermentation broth 864 is below the temperature of fermentation broth 861. Fermentation broth 864 may be returned to a fermentation vessel. Vapor stream 865 exits flash 851 and enters a spray tower 852 where it is contacted with droplets of absorption liquid 870. A residual vapor phase 866 exits the top of the spray tower 852. A portion 867 of the absorption liquid phase that exits the bottom of the spray tower 852 may be directed to distillation for recovery of product alcohol (e.g., butanol). The remaining portion of the absorption liquid is mixed with a regenerated absorption liquid 868 to form absorption liquid phase 869. Heat from absorption liquid phase 869 may be transferred into fermentation broth 860 using heat exchanger 854 resulting in absorption liquid phase 870 that may be recycled to the spray tower 852.

Additional heat may be supplied to the flash 851 via steam 863. This steam 863 may be derived at low pressure from an evaporation process that concentrates the thin stillage resulting from corn mash fermentation or from an evaporation process that concentrates the cane juice in sugar manufacturing. In a retrofitted thin stillage evaporation process, a train of eight evaporation bodies that are configured as two effects of four bodies in each effect may be reconfigured as four effects of two bodies in each effect. The vapor from the last effect may form low pressure steam 863.

The processes described herein may be used in a fermentation process utilizing feedstock and/or biomass derived from, but not limited to, corn, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. Also, any of the processes provided herein can be operated in conjunction with other vaporization processes, such as those described in PCT International Publication No. WO 2010/151832 A1.

Any of the processes provided herein can be operated and initiated at any time during a fermentation, and can be used to remove butanol or other product alcohol from a fermentation. In one embodiment, a process is initiated concurrently with initiation of a fermentation. In other embodiments, a process is initiated when the titer of product alcohol in the fermentation vessel is at least about 5 g/L, at least about 10 g/L, at least about 15 g/L, at least about 20 g/L, at least about 25 g/L, or at least about 30 g/L. In some embodiments, processes described herein are repeated throughout the course of the fermentation. In some embodiments, processes described herein are repeated such that the titer of product alcohol in the fermentation vessel is maintained at less than a preselected threshold.

EXAMPLES

Examples 1-4 were designed to determine the ability of certain absorption liquids to substantially reduce the volatility of carbon dioxide, isobutanol, and water. The selected absorption liquids were monoethanolamine (MEA), methyldiethanolamine (MDEA), and a mixture containing ethylene glycol and potassium carbonate. The reagents for these experiments are provided in Table 1. Example 5 is a comparative example without the absorption liquid.

A method known as the PTx method was used. Use of the PTx method is described in "Phase Equilibrium in Process Design," Wiley-Interscience Publisher, 1970, written by Harold R. Null, pages 124 through 126, hereby incorporated by reference. In the PTx method, the total absolute pressure in a cell of known volume is measured at a constant temperature for various known loading compositions.

TABLE 1

| Reagents | | | | | |
|---|---|---|---|---|---|
| Chemical name | CAS # | Purity | Supplier | Cat # | page |
| Methyl-diethanolamine (MDEA) | 105-59-9 | >99% | Aldrich | (Aldrich 2009-2010) 471828 | 1837 |
| 2-Methyl-1-propanol (I—BuOH) | 78-83-1 | 99.50% | Aldrich | 53132-1 L | 1908 |
| Potassium carbonate ($K_2CO_3$) | 584-08-7 | >99.0% | Aldrich | 209619-100 g | 2250 |

TABLE 1-continued

| Reagents | | | | | |
|---|---|---|---|---|---|
| Chemical name | CAS # | Purity | Supplier | Cat # | page |
| Ethylene Glycol | 107-21-1 | >99% | Aldrich | 102466-500 mL | 1289 |
| Mono-ethanolamine (MEA) | 141-43-5 | >99% | Aldrich | 398136-500 mL | 1246 |

Carbon dioxide for Examples 1-5 was Praxair product CD 4.0 IS-T with a specification of 99.99% carbon dioxide in the liquid phase (GTS/Welco, Allentown, Pa.).

Deionized water used in these experiments was from a stock supply. The conductivity of the deionized water was not believed to be relevant to the examples.

Figure 3:
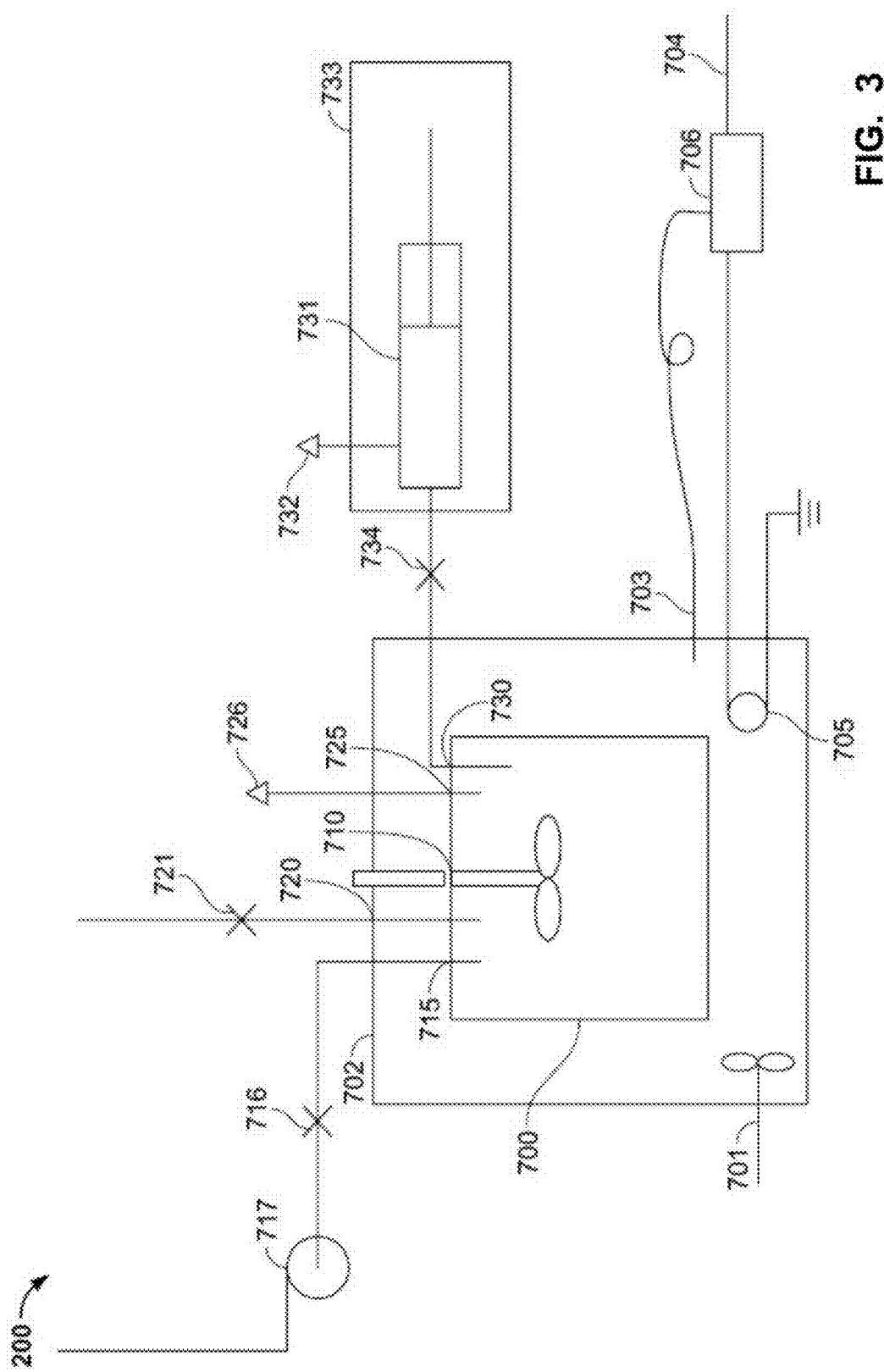
FIG. 3 is a schematic of the static cell PtX apparatus as described in Example 1.

A schematic diagram of a static cell PTx apparatus 200 is shown in FIG. 3. The 72.73 cm³ flanged sapphire static cell 700 was immersed in a stirred 701, electrically heated Syltherm-800® constant temperature bath 702 with a resistance temperature detector (RTD) 703, an electricity supply 704, a heater 705, and an Eurotherm 2604 temperature controller 706, which controlled temperature to ±0.01° C. The static cell contained a magnetically driven mixer 710.

This mixer 710 included a 6-bladed Rhuston turbine constructed of Hastelloy C. Gas was entrained through a center hole of the magnet, via a hollowed carbon bushing, to the hollow shaft. Circulation of gas down the shaft to two right angle holes, from the vapor space into the turbine was provided to accelerate attainment of an equilibrium between the liquid and gas.

This static cell was leak proof. A port 715 was connected through a valve 716 to a vacuum pump 717 (Gardner Denver Thomas, Inc., Welch Vacuum Technology, Niles, Ill.; model 1376N); a port 725 was connected to an accurate pressure transducer 726 (Druck model #PDCR330; Keller America, Inc., Newport News, Va.); and a port 730 was connected to a feed pump 731 for carbon dioxide. The $CO_2$ feed pump 731 (Model 87-6-5; High Pressure Equipment Company, Erie Pa.) was sufficiently accurate to supply a volume known to ±0.001 cm³ at the specified pressure. Pressure in the $CO_2$ feed pump 731 was measured with a pressure transducer 732 (Paro Scientific, Inc. Model 740; Redmond, Wash.). The $CO_2$ feed pump 731 was also in a temperature controlled water bath 733 and could be isolated from the static cell with a valve 734. All compositions are specified on a component to total weight basis unless otherwise noted.

Example 1

Absorption Liquid MEA

The pressure composition relationship at a known temperature was measured with the described apparatus 200 as follows:

51.967 grams of a mixture of 6.99% isobutanol, 20.01% deionized water, and 72.99% MEA were charged to static cell 700 and magnetically driven mixer 710 was started. The cell operating temperature was 44.42° C. and the liquid charge was 51.967 grams. The liquid mixture was degassed slowly by opening valve 716 connected to vacuum pump 717 until the cell pressure did not drop further. Valve 716 was then closed. The degas procedure was repeated until the cell pressure did not change with time when valve 716 to vacuum pump 717 was closed. The absence of leaks was verified by observing constant, below atmospheric pressure, in static cell 700 for at least 10 minutes. Cell 700 was heated to a targeted temperature with bath 702.

A measured volume of carbon dioxide at known pressure and temperature was introduced to cell 700 and the cell contents were agitated until the cell pressure remained constant. This cell pressure was noted. Additional carbon dioxide of known volume was added and a constant cell pressure was again noted. This step was repeated until a targeted quantity of carbon dioxide had been added. For the purpose of data analysis, the volume of carbon dioxide at known temperature and pressure was converted to mass using the reference, NIST 14, Thermodynamics and Transport Properties of Fluids, NIST Standard Reference Database 14, Version 4. Results are given in Table 2.

TABLE 2

Effect of MEA on vapor pressure

| Grams of $CO_2$ added to cell | Vapor pressure in cell - psia |
|---|---|
| 0 | 0.676 |
| 0.4912 | 0.735 |
| 0.9908 | 0.778 |
| 1.4971 | 0.826 |
| 1.9656 | 0.871 |
| 2.4939 | 0.922 |
| 3.1277 | 0.977 |
| 3.7217 | 1.024 |
| 4.3925 | 1.083 |
| 5.0284 | 1.137 |

Example 2

Absorption Liquid MEA

The procedures of Example 1 were repeated except the cell operating temperature was 44.46° C., the liquid composition was 7.24% isobutanol, 20.57% water, and 72.2% MEA, and the liquid charge was 49.925 grams. Results are given in Table 3.

TABLE 3

Effect of MEA on vapor pressure

| Grams of $CO_2$ added to cell | Vapor pressure in cell - psia |
|---|---|
| 0 | 0.684 |
| 0.0739 | 0.694 |
| 0.1577 | 0.705 |
| 0.2798 | 0.716 |
| 0.4121 | 0.724 |
| 0.5362 | 0.734 |
| 0.6657 | 0.742 |
| 0.8186 | 0.752 |
| 0.9679 | 0.761 |
| 1.1521 | 0.772 |

Example 3

Absorption Liquid MDEA

The procedures of Example 1 were repeated except the cell operating temperature was 44.45° C., the liquid composition was 4.99% isobutanol, 12.01% water, and 83% MDEA, and the liquid charge was 52.087 grams. Results are given in Table 4.

TABLE 4

Effect of MDEA on vapor pressure

| Grams of CO$_2$ added to cell | Vapor pressure in cell - psia |
|---|---|
| 0 | 0.654 |
| 0.0833 | 0.990 |
| 0.1678 | 1.5 |
| 0.3001 | 2.428 |
| 0.3966 | 3.153 |
| 0.5009 | 3.97 |
| 0.6058 | 4.812 |
| 0.7058 | 5.643 |
| 0.8164 | 6.579 |
| 0.9220 | 7.501 |

Example 4

Ethylene Glycol and Potassium Carbonate Mixture as Absorption Liquid

The procedures of Example 1 were repeated except the cell operating temperature was 44.52° C., the liquid composition was 6.86% isobutanol, 18.1% water, 9.04% potassium carbonate, and 66.01% ethylene glycol, and the liquid charge was 56.297 grams. Results are given in Table 5.

TABLE 5

Effect of ethylene glycol and potassium carbonate mixture on vapor pressure

| Grams of CO$_2$ added to cell | Vapor pressure in cell - psia |
|---|---|
| 0 | 0.886 |
| 0.08182 | 0.892 |
| 0.16689 | 0.898 |
| 0.30605 | 0.913 |
| 0.55314 | 0.953 |
| 0.80033 | 1.030 |
| 1.01325 | 1.163 |
| 1.39296 | 5.888 |
| 1.43120 | 10.145 |
| 1.46580 | 14.544 |

Comparative Example 5

Absence of Absorption Liquid

A control experiment was also performed in which CO$_2$ was added into deionized water using the same cell. The procedures of Example 1 were repeated except the cell operating temperature was 49.4° C., the liquid composition was 100% deionized water, and the liquid charge was 53.919 grams. Results are given in Table 6.

TABLE 6

Vapor pressure in the absence of absorption liquid

| Grams of CO$_2$ added to cell | Vapor pressure in cell - psia |
|---|---|
| 0 | 1.74 |
| 0.01689 | 5.00 |
| 0.12823 | 26.22 |
| 0.22952 | 45.71 |
| 0.33327 | 65.80 |
| 0.43932 | 86.38 |

TABLE 6-continued

Vapor pressure in the absence of absorption liquid

| Grams of CO$_2$ added to cell | Vapor pressure in cell - psia |
|---|---|
| 0.53909 | 105.85 |
| 0.64063 | 125.77 |
| 0.74679 | 146.77 |
| 0.84640 | 166.51 |
| 0.97062 | 191.26 |

The vapor pressure of the absorbent solutions used in Examples 1-4 were less than the vapor pressure of water alone from Example 5. Addition of even small amounts of carbon dioxide to water in the absence of absorption liquid, for example, 0.01223 grams in 53.919 grams of water, resulted in a substantial increase in the static cell pressure as can be seen in Example 5. Thus, an absorber containing water only, operating at near 45° C. and less than 2 psia, would condense only a small amount of carbon dioxide per unit of water absorption liquid. Some combination of refrigerated condensation and a compressor would be required to purge carbon dioxide from a vacuum flash with only water as an absorption liquid. An absorber containing ethylene glycol and potassium carbonate, or methyldiethanolamine absorption liquids, at concentrations above 70% would condense more carbon dioxide per unit of absorption liquid than the water would at about 45° C. and 2 psia. An absorbent containing monoethanolamine at a concentration of 70% to 75% would condense even more carbon dioxide per unit of scrubbing solution at near 45° C. and 2 psia and would require less absorbent per unit of carbon dioxide than the other Examples.

Example 6

Absorption and Desorption of CO$_2$: Absorption Liquid MEA

The purpose of this example was to demonstrate carbon dioxide absorption and then desorption in one of the absorbent solutions, monoethanolamine.

The example was developed using a 1.8 L HC60 Mettler RC1 agitated and jacketed calorimeter (Mettler-Toledo Mid Temp, Mettler-Toledo Inc., Columbus, Ohio) outfitted with a Mettler-Toledo REACT IR model 1000 In-Line FTIR using a DiComp, Diamond ATR Probe (Mettler-Toledo). The Diamond ATR probe was inserted into the RC1 reactor and sealed with a Swagelok fitting to form a pressure tight seal.

The pressure in the calorimeter was measured and recorded by an integrated Dynisco pressure transducer and RC press data recorder and control system. The weight of the CO$_2$ cylinder, the reactor content temperature, the jacket temperature, and the reactor pressures were likewise measured by components of the RC1 and recorded by the RC1 software. The weight of the CO$_2$ was determined to ±0.5 grams by displacement from a 2A cylinder.

Materials used in the calibration and absorption/desorption experiment described below were monoethanolamine (CAS No. 141-43-5; Catalog No. 398136; purity >99%; Sigma-Aldrich Corp., St. Louis, Mo.); 2-methylpropan-1-ol (CAS No. 78-83-1; Catalog No. 53132-1L; 99.50% purity; Sigma-Aldrich Corp.); and CO$_2$, 99.8% purity (Airgas East, Salem, N.H.; specification CGA G-6.2 Grade H).

Calibrating the FTIR

Seven hundred fifty grams (750.0 g) of a solution containing 547.5 g monoethanolamine, 52.5 g 2-methylpropan-1-ol, and 150.0 g deionized water were added to the RC1 calorimeter and heated to 45° C. while agitating at 600 rpm. The reaction solution was purged with 99.9999% pure nitrogen gas subsurface through a dip tube for 2 hours at a rate of 200 sccm. Nitrogen flow was stopped and the vessel was then pumped down to a pressure of 0.05 bar using a Welch model 1402 vacuum pump (Gardner Denver Thomas, Inc., Welch Vacuum Technology, Niles, Ill.). The degassed fluid in the evacuated and sealed reactor was then exposed to $CO_2$ at 0.10 bar and 45° C. The $CO_2$ was introduced into the reactor beneath the surface using a ⅛ inch diameter stainless steel dip tube. The $CO_2$ was added in 5 g aliquots until 35 g of $CO_2$ were absorbed. The FTIR spectra were allowed to line out before additional $CO_2$ was added at each 5 g increment.

Figure 4:
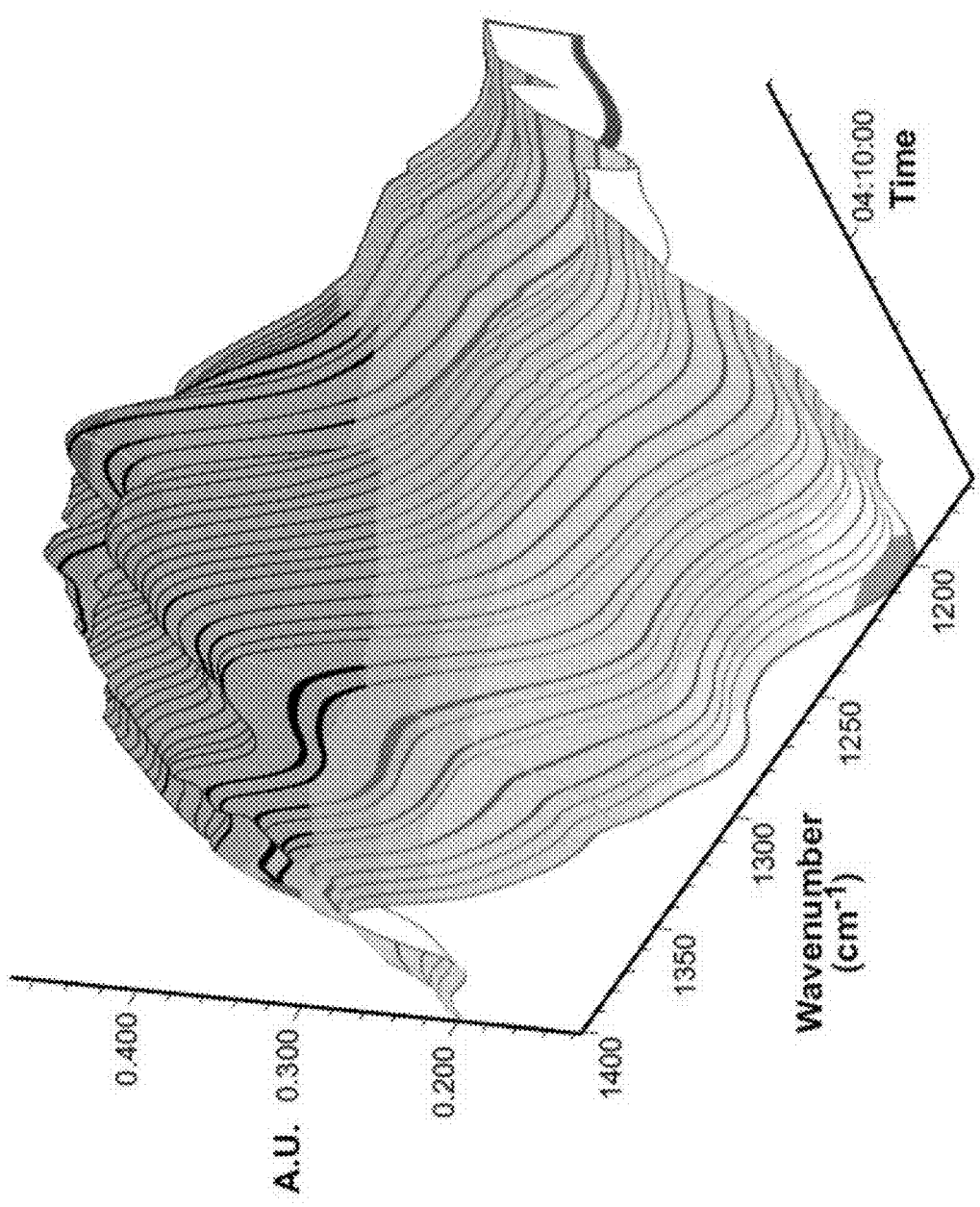
FIG. 4 is a graph of the peak height vs. $CO_2$ absorbed spectra for a monoethanolamine solution as described in Example 6.
Figure 5:
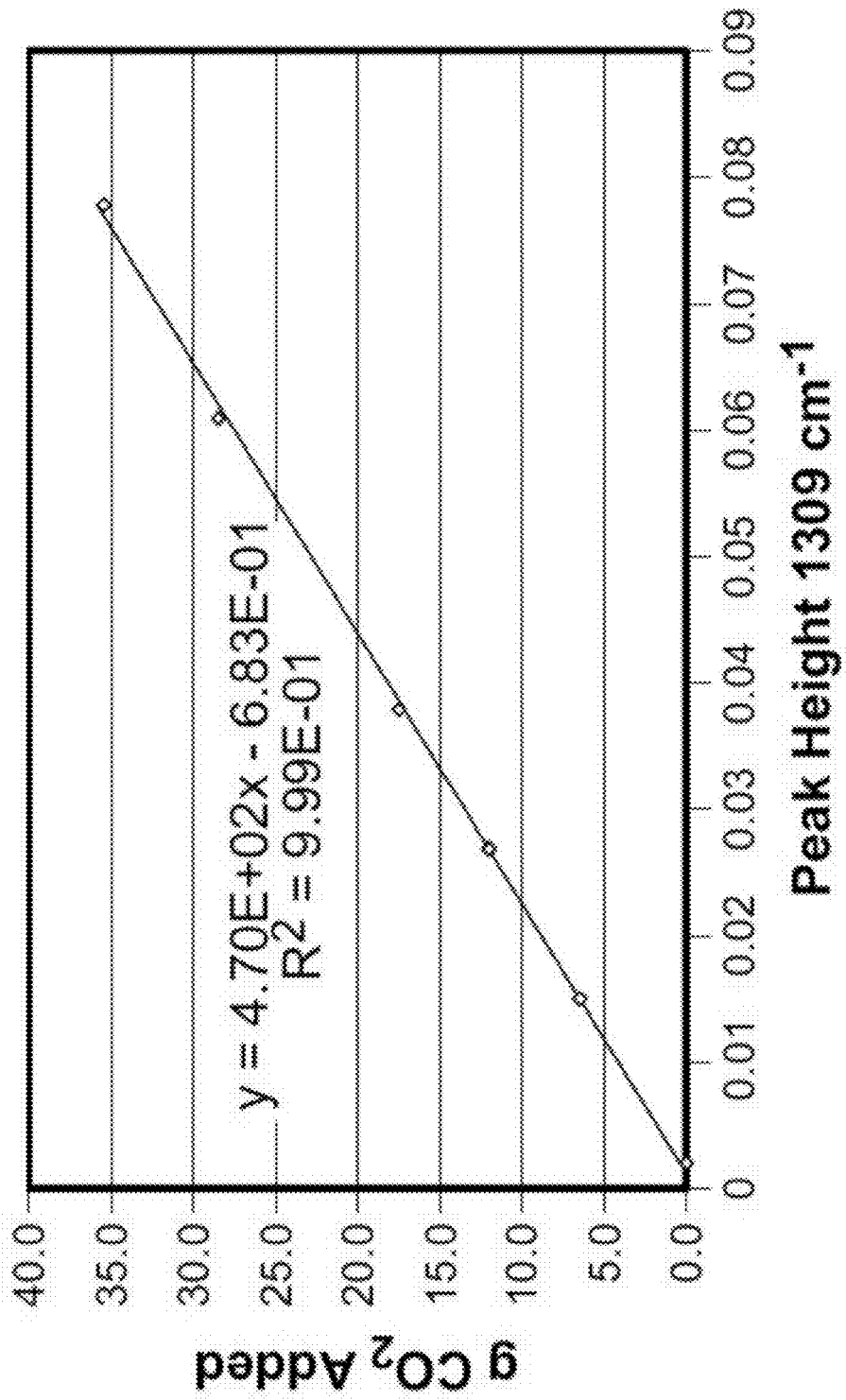
FIG. 5 is a graph of $CO_2$ absorbed vs. peak height as described in Example 6.

Mid-IR spectra were collected every 2 minutes during the experiments. The absorption of $CO_2$ into monoethanolamine forms a bicarbonate complex which has numerous IR absorbances (see FIG. 4). A band near 1309 $cm^{-1}$ was selected to follow the course of this experiment. A univariate approach was used to follow the 1309 $cm^{-1}$ peak with baselines drawn between 1341 $cm^{-1}$ and 1264 $cm^{-1}$. Absorbances to the two point baseline were used to create both the bicarbonate calibration plot and the temperature dependence plot. The $CO_2$ absorbed vs. peak height at 1309 $cm^{-1}$ is shown in FIG. 5.

Figure 6:
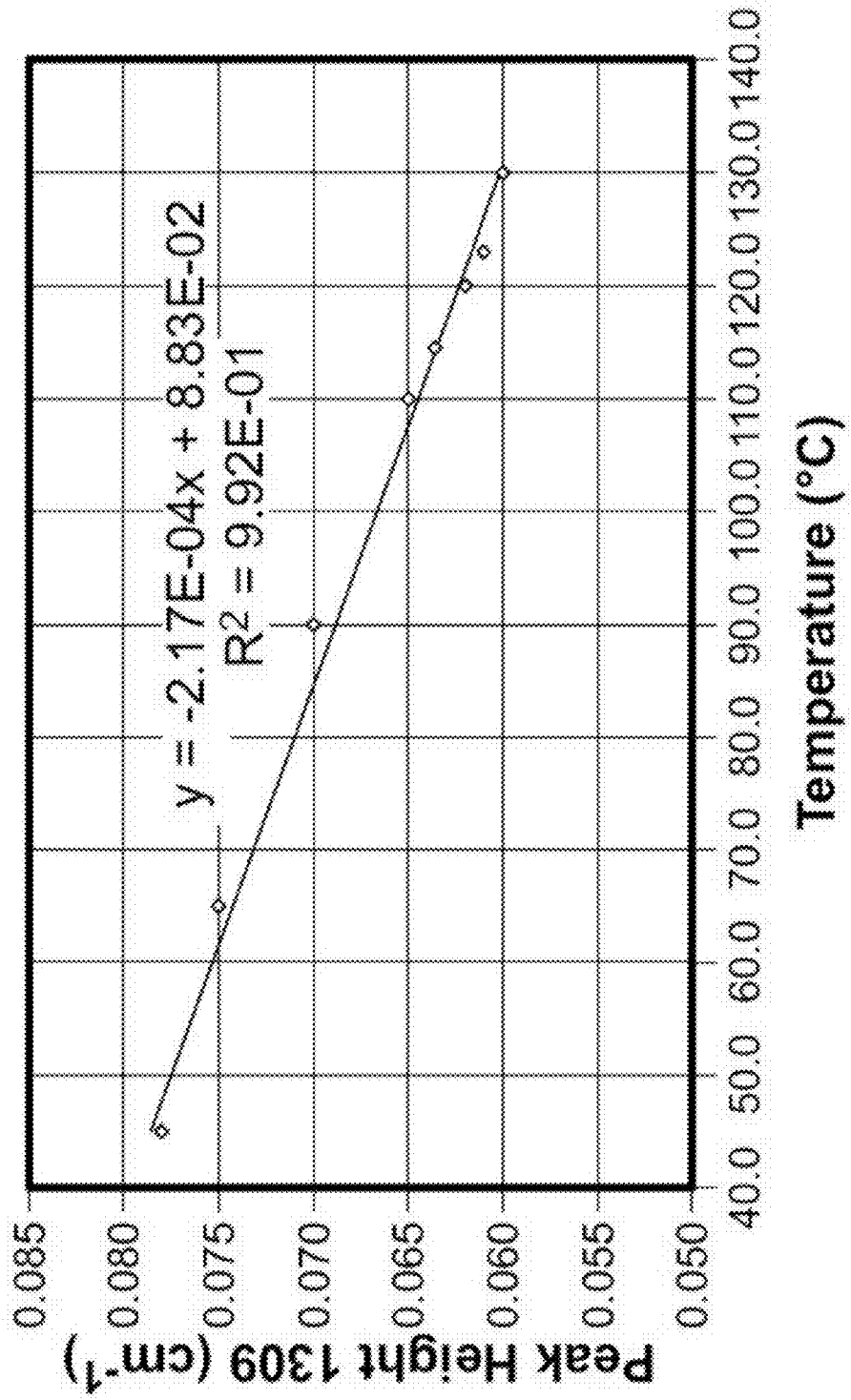
FIG. 6 is a graph of temperature vs. peak height as described in Example 6.

The solution with the absorbed $CO_2$ was heated in a sealed vessel and the peak height monitored throughout. A temperature vs. peak height calibration was generated and is shown in FIG. 6.

After the above calibration, an experiment was conducted to demonstrate absorption and desorption. Seven hundred fifty grams (750.0 g) of a solution containing 547.5 g monoethanolamine, 52.5 g 2-methylpropan-1-ol, and 150.0 g deionized water were added to the RC1 calorimeter at 45° C. while agitating at 800 rpm. The reaction solution was purged with 99.9999% pure nitrogen gas subsurface through a ¼ inch outside diameter, 0.18 ID dip tube for 2 hours at a rate of 200 sccm. The vessel was then pumped down to a pressure of 0.05 bar using a Welch model 1402 vacuum pump. The degassed fluid was exposed to carbon dioxide at 45° C. The $CO_2$ was introduced into the reactor beneath the surface using the ¼ inch outside diameter stainless steel dip tube. The $CO_2$ was taken up at a nearly constant rate of 6 g/min for nearly 6 minutes until a total of approximately 35 g of $CO_2$ was taken up into the reactor. The freeboard in the reactor was estimated to be about 0.75 liters and the amount of $CO_2$ in the vapor space under these conditions was calculated to be no more than 0.1 g, so that approximately 34.9 g of the 35 g was absorbed into the liquid solution. The pressure of the reactor was 70 mmHg after the $CO_2$ was added.

The reaction mass was heated to 150° C. at 1° C./min. As the temperature reached 118° C., the pressure was approximately 1.1 bar. A vent line was opened and vapor released from the reaction vessel into a vertically mounted condenser cooled with brine at −15° C. The bottom of the condenser contacted a separatory funnel, the bottom outlet of which was opened back to the vessel to maintain a constant temperature once the final desired reaction temperature was achieved by adjusting the boiling point of the solution in the reactor. In this way, $CO_2$ liberated from the monoethanolamine solution was vented from the process while the condensed liquids were returned. The vent line from the top of the vertically mounted condenser was attached to a bubbler and the formation of bubbles in the bubbler was an indication that $CO_2$ was being liberated from the reaction vessel. In addition, the in-line FTIR monitored the 1309 $cm^{-1}$ wavenumber peak indicative of the formation of a bicarbonate species or complex owing to the reaction of $CO_2$ and monoethanolamine. The FTIR peak profile indicated complete desorption of the $CO_2$ from the monoethanolamine peak in about 2.5 hours with over 60% of the desorbed $CO_2$ regenerated in about ½ hour. After 2.5 hours, the 1309 $cm^{-1}$ peak returned to its original base line value indicating all of the $CO_2$ had desorbed from the monoethanolamine solution. The bubbler also showed no signs of gas evolution after 2.5 hours.

This example demonstrates that an absorbent solution can be utilized to absorb carbon dioxide and then regenerated.

Example 7

ASPEN Model: Absorption Liquid Comprising Ethylene Glycol and Potassium Carbonate Processes described herein can be demonstrated using a computational model of the process. As described in U.S. Pat. No. 7,666,282, process modeling is an established methodology used by engineers to simulate complex chemical processes (and is incorporated herein by reference). The commercial modeling software Aspen Plus® (Aspen Technology, Inc., Burlington, Mass.) was used in conjunction with physical property databases, such as DIPPR, available from the American Institute of Chemical Engineers, Inc. (New York, N.Y.), to develop an ASPEN model of an integrated butanol fermentation, purification, and water management process.

Model inputs are defined in Table 7. A subset of this model illustrating the invention is best understood by reference to FIG. 7A which illustrates a flow diagram of a model process 300. Streams and outputs resulting from process 300 described are given in Tables 8A and 8B provided as FIGS. 7B and 7C, respectively. Batch fermentation was modeled as a steady state, continuous process using average flow rates.

Figure 7A:
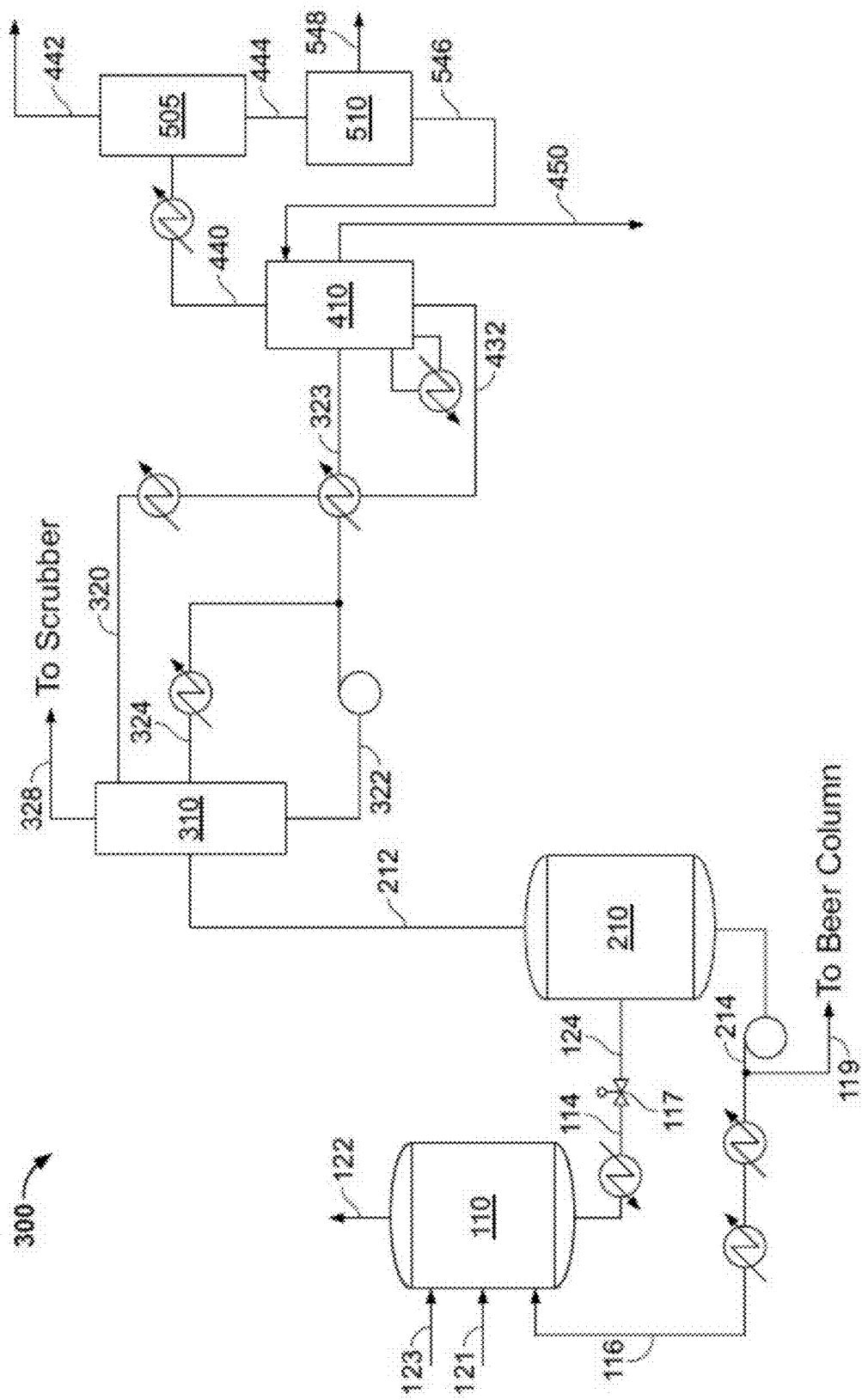
FIG. 7A is an example flow diagram for an embodiment of the processes provided and is referenced in Example 7.

With reference to FIG. 7A, mash stream 23MASH (123) and biocatalyst stream YEAST (121) are introduced to fermentation vessel 110. A vapor stream 112VAP (122), containing carbon dioxide, water, and butanol, is vented from the fermentation vessel 110 and directed to a butanol recovery scrubber (not shown). Beer stream 114BEER (114), heated to 31.4° C., is passed through a throttling valve 117, and is admitted into vacuum flash vessel 210 (which is a flash tank in this Example) as stream 113BEER (124). Flash tank 210 is at 0.1 bar which results in a portion of the beer flashing and a drop in temperature to 28° C. The flow rate and temperature of stream 113BEER (124) are selected to assure that the concentration of butanol in fermentation vessel 110 did not exceed 0.025 weight fraction. In this example, the ratio of butanol in a flashed beer stream 115BEER (214) compared to stream 113BEER (124) is 0.85.

Flashed beer stream 115BEER (214) is split into (i) a stream 24BEER (119), which simulates an average flow rate of a purge stream of nonfermentables and byproducts to additional butanol recovery systems (not shown) for butanol recovery, and (ii) a recycle stream 116REC (116) of yeast and unfermented sugars that is returned back to fermentation vessel 110.

A stream 67VENT (212), which is vapor from flash tank 210 enriched to 31.8 weight percent butanol and with a dewpoint of 28° C., is directed to vacuum absorption column 310 in which nearly all vapors are absorbed while operating with a bottoms temperature of 41.2° C. A stream VENT (328) including noncondensibles, and having near zero mass flow rate (in part representing air leaks into the vacuum equipment), is compressed and discharged to atmosphere through a water scrubber (not shown).

Vacuum absorption column 310 is supplied with two flows of absorbent, absorption liquid streams RICH1B (324) and LEAN (320). In this Example, the absorbent is ethylene glycol containing potassium carbonate and bicarbonate. Stream RICH1B (324) is absorbent re-circulated from the bottom of absorption column 310 after sufficient cooling to remove most or all of the heat of absorption. Stream LEAN (320) is absorbent returned from the regeneration process, described below, in sufficient quantity for assuring nearly complete absorption of carbon dioxide, butanol, and water. The combined bottoms stream RICH (322) is divided to supply stream RICH1B (324) and a stream RICH3 (323), which is diluted absorbent that is heated and directed to an absorbent regeneration column (serving as stripping column 410).

Regeneration column 410 is supplied heat at the base by indirect exchange with steam in sufficient quantity to vaporize almost all carbon dioxide and butanol, as well as sufficient water, to maintain a steady state composition. A column bottoms stream LEANT (432) is cooled, including in part by heat rejection to stream RICH3 (323) via a heat integration, and returned to absorption column 310 as stream LEAN (320).

A stream VAPOR (440) exits regeneration column 410 at one atmosphere and is partially condensed and separated (at vapor-liquid separator 505) to produce a stream COLVENT (442), which is a carbon dioxide purge that is discharged through a water scrubber (not shown). Condensate stream CONDENSE (444) is pumped (pump not shown) to condensate decanter vessel 510, combined with additional streams not described herein, and decanted. Decanter 510 generates an organic upper layer BUOH (548) which is sent to a butanol column (not shown) for purification and ultimately, commercial sales. A lower aqueous layer AQUEOUS (546) is returned as reflux to regeneration column 410. A liquid phase side draw is taken from regeneration column 410 between the reflux addition point and the feed addition point. This side draw stream WATEROUT (450) is pumped to the beer column (not shown) for further recovery of butanol.

TABLE 7

Model Inputs for Example 7

| Input | Value | Units |
|---|---|---|
| Production | 50 MM | gal per year |
| Backset | 15 | % |
| Corn Feed | | |
| Water Content | 15 | % |
| Corn Composition (dry) | | |
| STARCH | 70 | % |
| C5POLY | 5.2 | % |
| C6POLY | 3 | % |
| PROTEIN | 9.8 | % |
| OIL | 4 | % |
| NFDS | 8 | % |
| Waste from Milling | 0.3 | % |
| Misc Feeds to Mash | | |
| CIP | 2256 | kg/hr |
| Enzyme | 31.47 | kg/hr |
| CA | 53.6 | kg/hr |
| Ammonia | 89.8 | kg/hr |
| Mash Cooking | | |
| inlet mash temperature | 190 | deg F. |
| intermediate mash temperature approach to maximum temp | 18 | deg F. |
| Maximum mash temperature | 230 | deg F. |
| Saccharification | | |
| enzyme feed | 45.6 | kg/hr |
| acid feed | 21.1 | kg/hr |
| Starch Conversion | 99 | % |

TABLE 7-continued

Model Inputs for Example 7

| Input | Value | Units |
|---|---|---|
| Saccharifier Temp | 140 | deg F. |
| Saccharifier Pres | 40 | psia |
| Initial Cooldown approach to fermentation vessel temperature | 18 | deg F. |
| Fermentation Vessel | | |
| yeast feed | 8.5 | kg/hr |
| inlet temperature | 90 | deg F. |
| Glucose Conversion | 100 | % |
| NFDS Conversion | | |
| Fermentation vessel Temp | 90 | deg F. |
| Fermentation vessel Pres | 16 | psia |
| BuOH Titer | 25 | g/L |
| Flash tank pressure | 0.7 | psia |
| Flash tank liquid recirculation | 5061 | t/hr |
| $CO_2$ Degasser | | |
| Degasser pressure | 16 | psia |
| Degasser condenser temperature | 100 | deg F. |
| dT between degas temp and Beer Col bottoms cooler exit | 10 | deg C. |
| Beer Column | | |
| # of stages | 12 | |
| column pressures | | |
| Top | 20 | psia |
| Bottom | 21.5 | psia |
| feed stage locations | | |
| degassed liquid | stage 4 | |
| Condensate | stage 1 | |
| Aqueous reflux | stage 1 | |
| Butanol mass recovery | 99.65 | % |
| BuOH Column | | |
| # of stages | 10 | |
| column pressures | | |
| Top | 14.5 | psia |
| Bottom | 15.2 | psia |
| feed stage locations | | |
| Organic Reflux/Feed | Stage 1 | |
| Water in Bottom Product | 0.01 | % |
| BuOH Product Cooler | | |
| exit temp | 104 | deg F. |
| exit pres | 18.5 | psia |
| Scrubber | | |
| # of stages | 7 | |
| Pressure | 15 | psia |
| Centrifuge | | |
| solids/total flow in centrifuge tails | 0.287 | |
| Distiller's Dried Grains with Solubles (DDGS) dryer | | |
| water concentration in DDGS product | 9 | % |
| Evaporators | | |
| water concentration exit 4$^{th}$ evaporator | 60 | % |

TABLE 7-continued

Model Inputs for Example 7

| Input | Value | Units |
|---|---|---|
| 1st evaporator pressure | 5.37 | psia |
| 2nd evaporator temperature | 63.7 | deg C. |
| 3rd evaporator temperature | 53.2 | deg C. |

This Example demonstrates that the absorption temperature is 13° C. higher than the dew point of the vapor stream. Comparing stream 67VENT (212) to stream VENT (328) shows that more than 99% of the vapor stream including carbon dioxide is absorbed into the absorption. Furthermore, the Example demonstrates that the absorption liquid can be regenerated using processes described herein.

Example 8

ASPEN Model: Vaporization in Multi-Stage Distillation Column and Absorption Liquid Comprising Ethylene Glycol An ASPEN model of an integrated butanol fermentation, purification, and water management process was developed. The model inputs are given in Table 9. The model is described with reference to FIG. 8A, which illustrates a flow diagram of a model process 400. Streams and outputs resulting from process 400 described are given in Tables 10A and 10B provided as FIGS. 8B and 8C, respectively. Batch fermentation is modeled in this example as a steady state, continuous process using average flow rates.

Figure 8A:
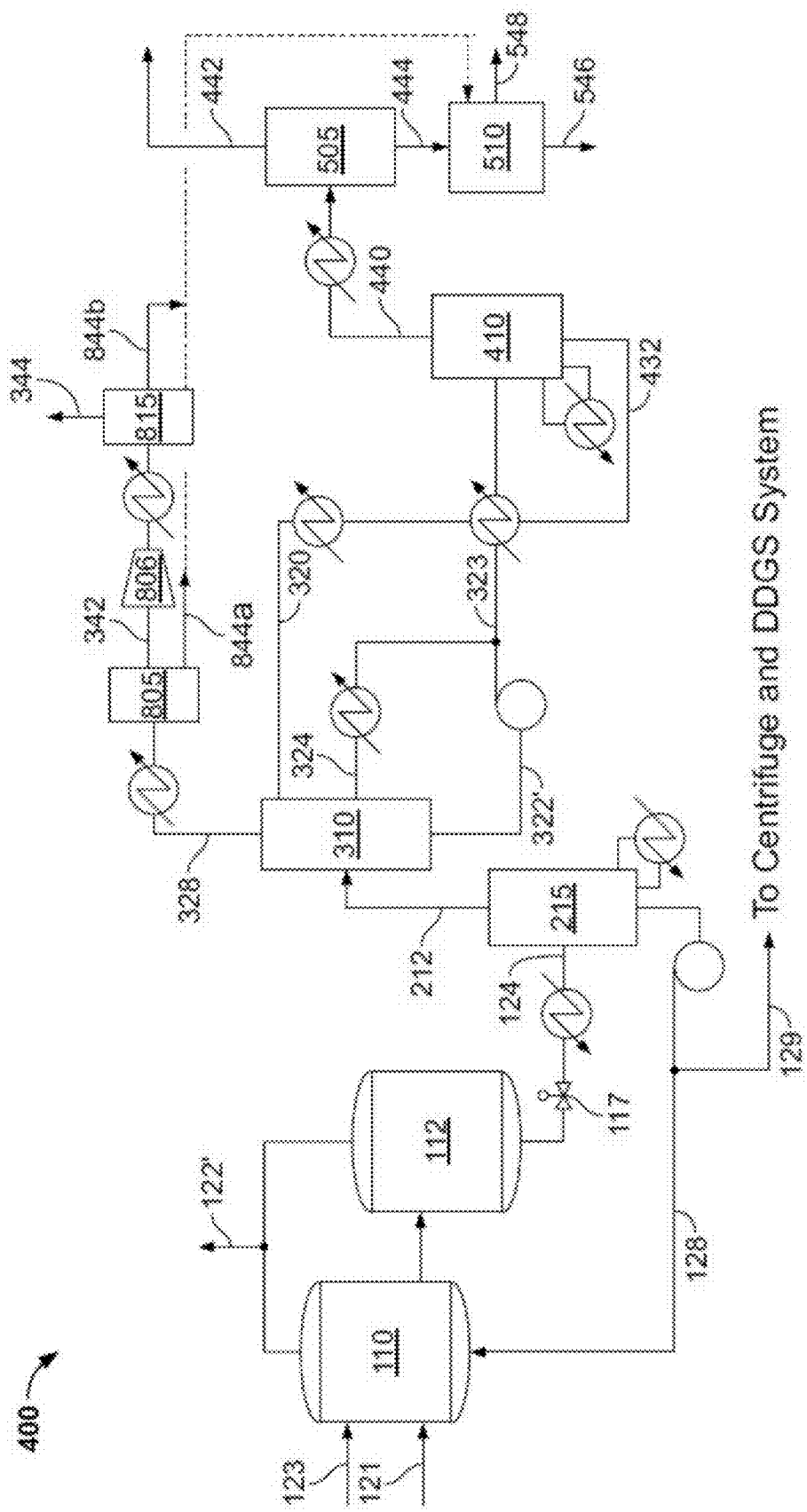
FIG. 8A is an example flow diagram for an embodiment of the processes provided and is referenced in Example 8.

With reference to FIG. 8A, mash stream 23MASH (123) and biocatalyst stream YEAST (121) are introduced to fermentation vessel 110. A vapor stream 68CO2 (122'), containing carbon dioxide, water, and butanol, is vented from fermentation vessel 110 and directed to a butanol recovery scrubber (not shown). Beer containing 25 grams per liter butanol is passed through an atmospheric disengagement tank 112 in which vapors from the beer are vented via a stream 68CO2 (122'), which is a stream combining the vented vapors from fermentation vessel 110 and disengagement tank 112. The circulated beer is then heated to form stream 26BEER (124), which is introduced into a vacuum flash multi-stage distillation column 215 (corresponding to vacuum flash vessel 210 of the process of FIG. 1). The pressure at the top of column 215 is at 0.07 atmospheres, and the butanol concentration in the gas stream is 34.5% by mass. Column 215 is indirectly heated. The number of stages of column 215, the heat input to column 215, and the flow rate of stream 26BEER (124) are selected to assure that the concentration of butanol in fermentation vessel 110 does not exceed the preselected threshold 0.025 weight fraction. Bottoms from vacuum flash column 215 containing 0.3 grams per liter butanol is split into (i) a stream 28RCY (128) that is returned to fermentation vessel 110 to ferment additional sugar to butanol, and (ii) a stream 29BEER (129) that is directed to a water recycle and Distiller's Dried Grains with Solubles (DDGS) production process (not shown). With the methods described herein, compounds that may be contaminating to DDGS are isolated from such co-product streams as opposed to other product removal processes and therefore, may provide additional benefit to fermentations comprising the product recovery methods described herein.

A vapor stream 30BOV (212) enriched to 34.5 weight percent butanol is directed from flash column 215 to vacuum absorption column 310. In absorption column 310, approximately 67% of the water plus butanol is absorbed from vapor stream 30BOV (212), but almost none of the carbon dioxide is absorbed. A vapor stream 328 from absorption column 310 is cooled, and a condensate stream 32COND (844a) is separated (at vapor-liquid separator 805) from residual vapors. From separator 805, a residual vapor stream 34VAP (342) is compressed, cooled again, and a condensate stream 38COND (844b) is separated (at vapor-liquid separator 806) from residual vapors which form a stream 40VAP (344) that is directed to a water scrubber (not shown).

Vacuum absorption column 310 is supplied with two flows of absorbent, absorption liquid streams 324 and 320. In this Example, the absorbent is ethylene glycol (glycol) without potassium carbonate or other base. Stream 324 is absorption liquid re-circulated from the bottom of absorption column 310 after sufficient cooling to remove most or all of the heat of absorption. Stream 320 is absorption liquid returned from the regeneration process, described below. The combined bottoms stream 322' is divided to supply stream 324 and stream 323. Stream 323 is diluted absorption liquid (or solution rich with solutes) which is heated and directed to absorption regeneration column 410.

Absorption regeneration column 410 is supplied heat at the base by indirect exchange with steam in sufficient quantity to vaporize butanol and water to maintain a steady state composition. Column bottoms stream 432 is cooled, including in part by heat rejection to stream 323 via a heat integration, and returned as stream 320 to absorption column 310.

Vapor stream 440 exits regeneration column 410 at one atmosphere and is combined with other vapors and partially condensed and separated (at vapor-liquid separator 505) to produce stream COLVENT (442), which is a carbon dioxide purge that is discharged through a water scrubber (not shown). Condensate stream CONDENSE (444) is pumped (pump not shown) to condensate decanter vessel 510, combined with additional streams not described herein, and decanted. Decanter 510 generates an organic upper layer 47ORG (548) which is sent to a butanol column (not shown) for purification and ultimately, commercial sales. A lower aqueous layer 48AQ (546) is in part returned as reflux (not shown) to flash column 215 and in part used as reflux (not shown) for regeneration column 410.

TABLE 9

Model Inputs for Example 8

| Input | Value | Units |
|---|---|---|
| Production | 50 MM | gal per year |
| Backset | 15 | % |
| Corn Feed | | |
| Water Content | 15 | % |
| Corn Composition (dry) | | |
| STARCH | 70 | % |
| C5POLY | 5.2 | % |
| C6POLY | 3 | % |
| PROTEIN | 9.8 | % |
| OIL | 4 | % |
| NFDS | 8 | % |
| Waste from Milling | 0.3 | % |
| Misc Feeds to Mash | | |
| CIP | 2256 | kg/hr |
| Enzyme | 31.47 | kg/hr |
| CA | 53.6 | kg/hr |
| Ammonia | 89.8 | kg/hr |

TABLE 9-continued

Model Inputs for Example 8

| Input | Value | Units |
|---|---|---|
| Mash Cooking | | |
| inlet mash temperature | 190 | Deg F. |
| intermediate mash temperature approach to maximum temp | 18 | Deg F. |
| Maximum mash temperature | 230 | Deg F. |
| Saccharification | | |
| enzyme feed | 45.6 | kg/hr |
| acid feed | 21.1 | kg/hr |
| Starch Conversion | 99 | % |
| Saccharifier Temp | 140 | Deg F. |
| Saccharifier Pres | 40 | psia |
| Initial Cooldown approach to fermentation vessel temperature | 18 | Deg F. |
| Fermentation vessel | | |
| yeast feed | 8.5 | kg/hr |
| inlet temperature | 90 | Deg F. |
| Glucose Conversion | 100 | % |
| NFDS Conversion | | |
| Fermentation vessel Temp | 90 | Deg F. |
| Fermentation vessel Pres | 16 | psia |
| BuOH Titer | 25 | g/L |
| Two Stage Compressor/Condenser | | |
| First stage pressure | 4 | psia |
| Second stage pressure | 16 | psia |
| Vacuum condenser temperature | 30 | Deg C. |
| Beer Column | | |
| # of stages | 6 | |
| column pressures | | |
| Top | 1 | psia |
| Top condenser temperature | 30 | deg C. |
| feed stage locations | | |
| stream from fermentation vessel | Stage 1 | |
| aqueous reflux | Stage 1 | |
| Butanol mass recovery | 99 | % |
| EG Absorber | | |
| # of stages | 5 | |
| Top P | 0.8 | psia |
| EG Feed | Stage 1 | |
| Beer vapor feed | Stage 5 | |
| BUOH Regeneration Col | | |
| # of stages | 15 | |
| Top P | 1 | atm |
| Reflux Aqueous phase from decanter | stage1 | |
| Bottom IBA spec | 100 | ppm |
| BuOH Column | | |
| # of stages | 8 | |
| column pressures | | |
| Top | 20 | psia |
| Bottom | 22 | psia |
| feed stage locations | | |
| Organic Reflux/Feed | Stage 1 | |
| BuOH in bottoms | 99.55 | % |
| BuOH Product Cooler | | |
| exit temp | 104 | Deg F. |
| exit pres | 18.5 | psia |
| Scrubber | | |
| # of stages | 6 | |
| Pressure | 15 | psia |
| Centrifuge | | |
| solids/total flow in centrifuge tails | 0.287 | |

TABLE 9-continued

Model Inputs for Example 8

| Input | Value | Units |
|---|---|---|
| DDGS dryer | | |
| water concentration in DDGS product | 9 | % |
| Evaporators | | |
| water concentration exit 4th evaporator | 45 | % |
| 1st evaporator pressure | 20 | psia |
| 2nd evaporator temperature | 99 | Deg C. |
| 3rd evaporator temperature | 88 | Deg C. |
| 4th evaporator temperature | 78 | Deg C. |

This Example shows that use of a multi-stage distillation column can reduce the amount of carbon dioxide removed with butanol while maintaining the butanol concentration at or below a preselected threshold of 2.5 mass percent in the fermentation tank. Also, the multi-stage distillation column is operated such that the butanol concentration in the column feed is more than 80 times greater than that in the bottoms stream returned to the fermentation vessel. Furthermore, use of an absorption liquid, for example, ethylene glycol is used without a base, allows absorption of approximately 65% by mass of the sub-atmospheric vapor at an initial condensation temperature of 40.9° C., which is higher than the initial condensation temperature of the sub-atmospheric vapor stream in the absence of an absorption liquid, that is, 37.7° C.

Example 9

Multi-Stage Distillation Column Example—No Absorption Step

An ASPEN model of an integrated butanol fermentation, purification, and water management process 500 was developed and is described with reference to FIG. 9A. All flow rates were modeled as time averages even though they may be non-continuous. Model inputs are given in Table 11, and results are given in Tables 12A and 12B provided as FIGS. 9B and 9C, respectively.

Figure 9A:
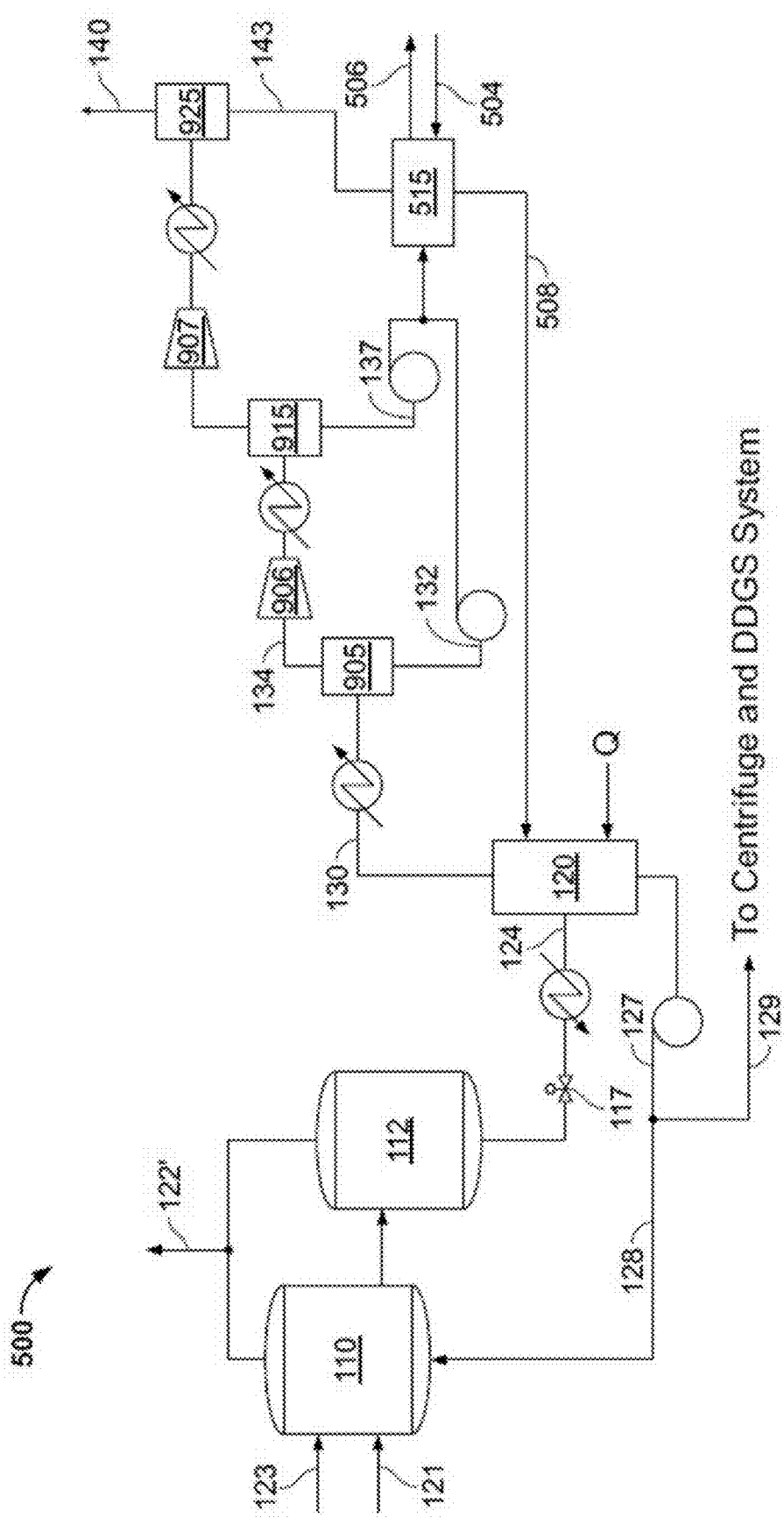
FIG. 9A is an example flow diagram for an embodiment of the processes provided and is referenced in Example 9.

With reference to FIG. 9A, mash and nutrients stream 23MASH (123) and biocatalyst YEAST stream (121) are introduced to fermentation vessel 110. Vapor stream 68CO2 (122') containing carbon dioxide, water, and butanol is vented from fermentation vessel 110 and directed to a butanol recovery scrubber (not shown). Beer is circulated from fermentation vessel 110 to a vacuum beer column 120 (via atmospheric disengagement tank 112) at sufficient rates to assure that the butanol concentration in the beer does not exceed a preselected threshold target, in this case 2.5% by weight. In atmospheric disengagement tank 112, vapors from the beer are vented and combined with vapor stream 68CO2 (122'). The circulated beer is then heated to form stream 26BEER (124), which is introduced into multi-stage, sub-atmospheric beer column 120. The feed point and the number of stages can be optimized by those familiar with the state of the art of beer column design. In this model, the number of theoretical stages in beer column 120 is 6 and the feed is to stage 1. Sufficient heat is added at the bottom of beer column 120 in the form of low pressure steam to reduce the butanol content of the beer by more than 98%. In this example, the pressure at the top of column 120 is 1 psia.

A beer column bottoms stream 27BOT (127) is substantially stripped of butanol in beer column 120, and a portion of stream 27BOT (127) (about 70%) is returned to fermentation vessel 110 as recycle stream 28RCY (128) for further conversion of carbohydrates to butanol. The remainder of the stripped beer, stream 29BEER (129), is sent to a DDGS system (not shown) of the types known in the art as may be necessary to control accumulation of suspended solids and other impurities.

A vapor stream 30BOV (130) from beer column 120, enriched in butanol, is cooled, and a liquid condensate stream 32COND (132) and a vapor stream 34VAP (134) are separated in a vacuum vapor-liquid separator 905. The remaining vapor is conveyed through a compressor train, in which it is compressed, cooled, and separated two times (at respective compressor 906, vapor-liquid separator 915, compressor 907, and vapor-liquid separator 925) to produce additional condensate streams 37COND (137) and 43COND (143) from separators 915 and 925. A residual vapor stream 40VAP (140) from this compressor train is above atmospheric pressure and is routed to a water scrubber (not shown) before discharge to the atmosphere. Condensate streams 32COND (132), 37COND (137), and 43COND (143) are combined with additional streams not described herein, and decanted in a decanter 515. A water rich lower phase 508 from decanter 515 is returned to beer column 120. An organic rich upper phase 506 from decanter 515 is sent to a butanol recovery column (not shown) for purification, and ultimately, commercial sales.

TABLE 11

Model Inputs for Example 9

| Input | Value | Units |
|---|---|---|
| Production | 50 MM | gal per year |
| Backset | 15 | % |
| Corn Feed | | |
| Water Content | 15 | % |
| Corn Composition (dry) | | |
| STARCH | 70 | % |
| C5POLY | 5.2 | % |
| C6POLY | 3 | % |
| PROTEIN | 9.8 | % |
| OIL | 4 | % |
| NFDS | 8 | % |
| Waste from Milling | 0.3 | % |
| Misc Feeds to Mash | | |
| CIP | 2256 | kg/hr |
| Enzyme | 31.47 | kg/hr |
| CA | 53.6 | kg/hr |
| Ammonia | 89.8 | kg/hr |
| Mash Cooking | | |
| inlet mash temperature | 190 | deg F. |
| intermediate mash temperature approach to maximum temp | 18 | deg F. |
| Maximum mash temperature | 230 | deg F. |
| Saccharification | | |
| enzyme feed | 45.6 | kg/hr |
| acid feed | 21.1 | kg/hr |
| Starch Conversion | 99 | % |
| Saccharifier Temp | 140 | deg F. |
| Saccharifier Pres | 40 | psia |
| Initial Cooldown approach to fermentation vessel temperature | 18 | deg F. |
| Fermentation vessel | | |
| yeast feed | 8.5 | kg/hr |
| inlet temperature | 90 | deg F. |
| Glucose Conversion | 100 | % |

TABLE 11-continued

Model Inputs for Example 9

| Input | Value | Units |
|---|---|---|
| NFDS Conversion | | |
| Fermentation vessel Temp | 90 | deg F. |
| Fermentation vessel Pres | 16 | psia |
| BuOH Titer | 25 | g/L |
| Two Stage Compressor/Condenser | | |
| First stage pressure | 4 | psia |
| Second stage pressure | 16 | psia |
| Vacuum condenser temperature | 30 | deg C. |
| Beer Column | | |
| # of stages | 6 | |
| column pressures | | |
| Top | 1 | psia |
| Top condenser temperature | 30 | deg C. |
| feed stage locations | | |
| stream from fermentation vessel | stage 1 | |
| aqueous reflux | stage 1 | |
| Butanol mass recovery | 99 | % |
| BuOH Column | | |
| # of stages | 8 | |
| column pressures | | |
| Top | 20 | psia |
| Bottom | 22 | psia |
| feed stage locations | | |
| Organic Reflux/Feed | Stage 1 | |
| BuOH in bottoms | 99.55 | % |
| BuOH Product Cooler | | |
| exit temp | 104 | deg F. |
| exit pres | 18.5 | psia |
| Scrubber | | |
| # of stages | 6 | |
| Pressure | 15 | psia |
| Centrifuge | | |
| solids/total flow in centrifuge tails | 0.287 | |
| DDGS dryer | | |
| water concentration in DDGS product | 9 | % |
| Evaporators | | |
| water concentration exit 4th evaporator | 45 | % |
| 1st evaporator pressure | 20 | psia |
| 2nd evaporator temperature | 99 | deg C. |
| 3rd evaporator temperature | 88 | deg C. |
| 4th evaporator temperature | 78 | deg C. |

This Example demonstrates that efficient stripping of butanol in the beer column permits a flow rate allowing 20002 kg/h of $CO_2$ to vent from fermentation vessel 110 and optional atmospheric flash tank (i.e., atmospheric disengagement tank 112) compared to only 961 kg/h through sub-atmospheric beer column 120 and compressor train. Consequently, the compressor is smaller and will require less energy than if a higher fraction of the $CO_2$ were vented from sub-atmospheric beer column 120. Also, the multi-stage distillation beer column 120 is operated such that the butanol mass in the bottoms stream 127 is about 1% of the butanol mass in the feed stream 124.

Example 10

Air Stripping before Vacuum Flash

An ASPEN model of an integrated butanol fermentation, purification, and water management process 700 was developed and is described with reference to FIG. 10A. All flow rates were modeled as time averages even though they may be non-continuous. Model inputs are given in Table 13, and results are given in Tables 14A and 14B provided as FIGS. 10B and 10C, respectively.

Figure 10A:
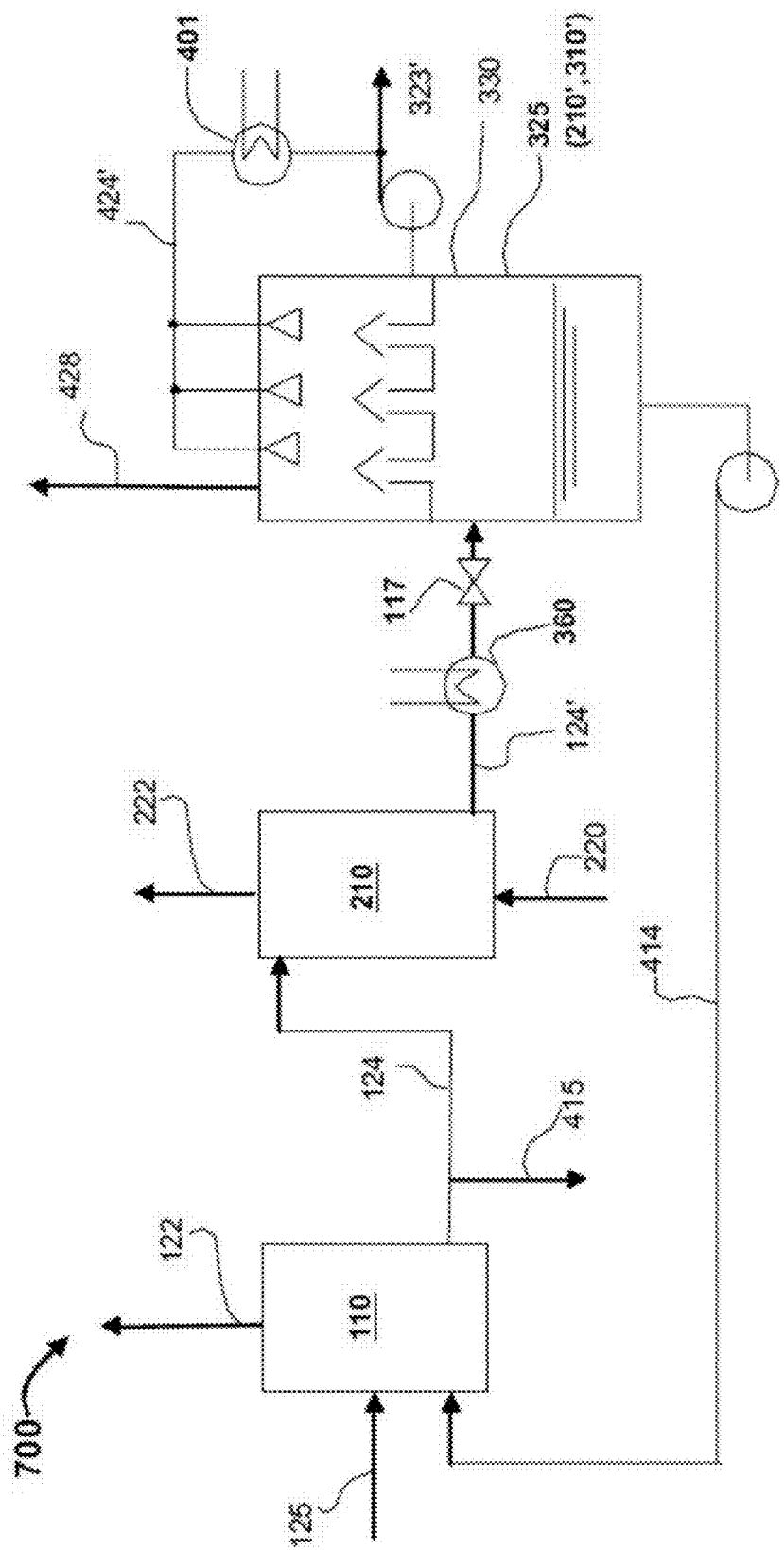
FIG. 10A illustrates an example system useful for practicing processes according to embodiments described herein, and specifically for demonstrating air stripping before vacuum flash.

With reference to FIG. 10A, mash and nutrients stream 125 and biocatalyst (not shown) are introduced to fermentation vessel 110. A vapor stream 122 containing carbon dioxide, water, and butanol are vented from fermentation vessel 110 and directed to a butanol recovery scrubber (not shown). Beer is circulated from fermentation vessel 110. A portion 415 is directed to a beer column (not shown) to purge non-fermentables. A portion 124 is directed to an air stripper 210 at sufficient rates to assure that the butanol concentration in the beer does not exceed a preselected threshold target, in this case 2.5% by weight. Carbon dioxide is stripped from the beer in a three stage column provided 2308 kg/h of air. The stripping gas flow rate and the number of stages can be optimized by those familiar with the stripping column design. Sufficient heat is added by heater 360 to maintain the temperature of flash tank 325 (described below) at 32° C. The beer is passed through throttling valve 117 into the lower compartment of vessel 325 where it is allowed to flash at a pressure of 0.05 atm, causing the vaporization of butanol, carbon dioxide, and water. These vapors, enriched in butanol, pass into compartment 310' of vessel 325 were they are partially condensed at 20° C. Condensate is removed from 310' and pumped through a cooler 401 and returned by stream 424' to maintain the condensation temperature. A portion of the condensate 323' is removed from the circulation loop and further processed to produce product butanol and water suitable for recycle in facilities not shown. The remaining vapor stream 428 is conveyed through a compressor train, in which it is compressed, cooled, and separated two times as described in Example 8.

Beer not flashed in the flash tank is pumped (not shown) by stream 414 to return nutrients to the fermentation vessel for further fermentation.

TABLE 13

Model Inputs for Example 10

| Input | Value | Units |
|---|---|---|
| Production | 40 MM | gal per year |
| Backset | 15 | % |
| Corn Feed | | |
| Water Content | 15 | % |
| Corn Composition (dry) | | |
| STARCH | 70 | % |
| C5POLY | 5.2 | % |
| C6POLY | 3 | % |
| PROTEIN | 9.8 | % |
| OIL | 4 | % |
| NFDS | 8 | % |
| Waste from Milling Fermentation vessel | 0.3 | % |
| yeast feed | 8.5 | kg/hr |
| inlet temperature | 90 | deg F. |
| Glucose Conversion | 100 | % |

TABLE 13-continued

Model Inputs for Example 10

| Input | Value | Units |
|---|---|---|
| NFDS Conversion | | |
| Fermentation vessel Temp | 90 | deg F. |
| Fermentation vessel Pres | 16 | psia |
| BuOH Titer | 25 | g/L |
| Air Stripper | | |
| Stages | 3 | |
| Air flow rate | 2308 | Kg/h |
| Flash Tank | | |
| Pressure | 0.05 | Atm |
| Inlet Temperature | 31.8 | deg C. |
| Condenser temperature | 20 | deg C. |

This Example demonstrates that air stripping of beer after the fermentation vessel and prior to flashing will reduce the $CO_2$ content in the vapor from the flash. Consequently, the vapors from the flash may be more completely condensed at temperatures on the order of 20° C.

Example 11

Recycle of Decanted Water

Figure 12:
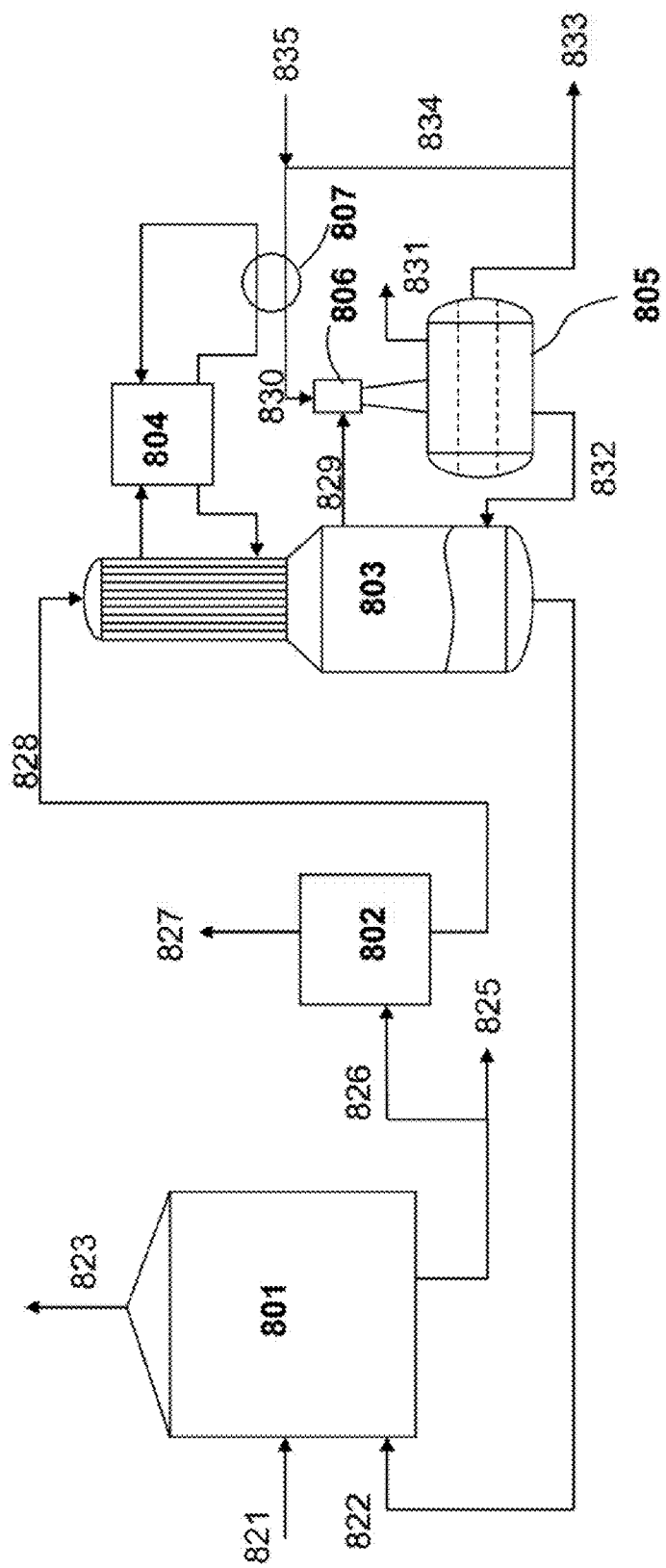
FIG. 12 illustrates an example system useful for practicing processes according to embodiments described herein.

An ASPEN model of an integrated butanol fermentation, purification, and water management process was developed and is described with reference to FIG. 12. All stream flows are intended to quantify an average steady state operation basis. Model inputs are given in Table 15, and results are given in Tables 16A and 16B.

A stream of liquefied mash 821 including suspended solids and dissolved fermentable starch at a temperature of 32° C. is fed to a fermentation vessel 801. Fermentation vessel 801 may comprises one, two, three, four, or more fermentation vessels. A vapor stream 823 comprised predominantly of carbon dioxide exits from the top of the fermentation vessel 801. At any time, the fermentation vessel 801 is circulating fermentation broth contents through a loop that involves two stages of pressure reduction. Stream 826 is representative of the combined average loop flow for the fermentation vessel 801. Stream 825 is representative of the combined average flow of fermentation broth that has been depleted of fermentable sugars. The circulation flowing to the first-stage flash 802 is stream 826. The liquid fraction of stream 826 comprises 1.4 wt % dissolved isobutanol and 0.23 wt % dissolved carbon dioxide. Exiting a first-stage flash 802 is a vapor stream 827 that is comprised predominantly of carbon dioxide. The fermentation broth 828 from the first-stage flash comprises 0.03 wt % dissolved carbon dioxide and is transferred to a falling film evaporator 803. The falling film evaporator 803 also receives an aqueous stream 832. Exiting the falling film evaporator 803 is a vapor stream 829 at a temperature of 29.3° C. and 0.6 psia and a fermentation broth 822 comprising 1.0 wt % isobutanol. The fermentation broth 822 is pumped back to the fermentation vessel 801. The vapor stream 829 is drawn into an ejector-venturi scrubber 806 by the draft induced by the velocity of stream 830 comprising 2-ethyl hexanol entering at 27° C. and the mixture discharges into settling tank 805. A vapor stream 831 exits this settling tank 805. An aqueous stream 832 decanted off the bottom of this settling tank 805 is transferred back to the falling film evaporator 803 directly. An organic stream exits from this settling tank 805, a portion of which is pumped over to a distillation area for regeneration of 2-ethyl hexanol that is lean in isobutanol. A larger portion 834 is combined with regenerated absorption liquid 835 and is circulated through a heat exchanger 807 to transfer its heat back to the falling film evaporator 803 via a heat pump refrigeration system 804.

TABLE 16A

| Stream | 821 | 822 | 823 | 825 | 826 | 827 | 828 |
|---|---|---|---|---|---|---|---|
| Total Flow kg/hr | 181904 | 3020240 | 10789.88 | 144277 | 3047080 | 6268.168 | 3040820 |
| Vapor/liquid phases | | | | | | | |
| Mass Flow kg/hr | | | | | | | |
| $CO_2$ | 0 | 1.00828 | 10646.27 | 344.8676 | 6552.485 | 5695.88 | 856.6054 |
| WATER | 134552 | 2391330 | 105.1603 | 126283 | 2399370 | 421.4974 | 2398950 |
| GLYCEROL | 563.9827 | 34918.44 | 6.22838E−07 | 1837.813 | 34918.44 | 2.33201E−06 | 34918.44 |
| I-BUOH | 0.00680223 | 28700.74 | 38.4513 | 2155.438 | 40953.33 | 150.7765 | 40802.55 |
| CORNOIL | 1442.135 | 27399.5 | 0.000174881 | 1442.082 | 27399.55 | 0.000529318 | 27399.55 |
| ISOOCTYL | 0 | 3.351294 | 0.0035356 | 0.1673881 | 3.180375 | 0.013521 | 3.166853 |
| GLUCOSE | 0 | 0 | 0 | 0 | 0 | 0 | 0 |
| PROTEIN | 779.0843 | 14802.6 | 1.0683E−12 | 779.0843 | 14802.6 | 2.9497E−12 | 14802.6 |
| KCL | 146.997 | 2792.944 | 2.0087E−13 | 146.997 | 2792.944 | 5.5626E−13 | 2792.944 |
| $CASO_4$ | 146.997 | 2792.944 | 2.0166E−13 | 146.997 | 2792.944 | 5.5659E−13 | 2792.944 |
| DAP | 807.2722 | 2087.248 | 1.5067E−13 | 109.8551 | 2087.248 | 4.1594E−13 | 2087.248 |
| MAP | 64.82303 | 11949.24 | 8.6162E−13 | 628.9076 | 11949.24 | 2.3808E−12 | 11949.24 |
| STARCH | 33980.51 | 305825 | 2.1013E−11 | 0 | 305825 | 6.0961E−11 | 305825 |
| Total Flow kg/hr | 172483 | 2822610 | 10789.88 | 133875 | 2849450 | 6268.168 | 2843180 |
| Temperature C. | 32 | 29.35706 | 31.99999 | 31.99999 | 32.00023 | 31.6897 | 31.6897 |
| Pressure psia | 29.392 | 29.392 | 29.392 | 29.392 | 29.392 | 4.4088 | 4.4088 |
| Suspended solids Mass Flow kg/hr | | | | | | | |
| PROTEIN | 3586.513 | 68143.75 | 0 | 3586.513 | 68143.75 | 0 | 68143.75 |
| STARCH | 205.1137 | 3897.161 | 0 | 205.1137 | 3897.161 | 0 | 3897.161 |
| FIBER | 5600.806 | 106415 | 0 | 5600.806 | 106415 | 0 | 106415 |
| YEAST | 28.15887 | 19181.5 | 0 | 1009.553 | 19181.5 | 0 | 19181.5 |
| Total Flow kg/hr | 9420.592 | 197638 | 0 | 10401.99 | 197638 | 0 | 197638 |

TABLE 16B

| Stream | 829 | 830 | 831 | 832 | 833 | 834 | 835 |
|---|---|---|---|---|---|---|---|
| Total Row kg/hr | 61442.15 | 1561720 | 2042.168 | 40870.56 | 316050 | 1264200 | 297520 |
| Vapor/liquid phases | | | | | | | |
| Mass Flow kg/hr | | | | | | | |
| $CO_2$ | 857.465 | 498.8253 | 730.891 | 1.867861 | 124.7063 | 498.8253 | 0 |
| WATER | 48355.78 | 48741.42 | 1058.696 | 40741.47 | 11059.41 | 44237.62 | 4503.8 |
| GLYCEROL | 0.000217639 | 0.000240348 | 1.6221E−11 | 0.000157552 | 6.00869E−05 | 0.000240348 | 0 |
| I-BUOH | 12227.21 | 47914 | 123.3111 | 125.4027 | 11978.5 | 47914 | 0 |
| CORNOIL | 0.0532469 | 0.2129879 | 1.5222E−10 | 6.02305E−09 | 0.0532469 | 0.2129879 | 0 |
| ISOOCTYL | 1.631575 | 1464567 | 129.2698 | 1.816015 | 292887 | 1171550 | 293017 |
| GLUCOSE | 0 | 0 | 0 | 0 | 0 | 0 | 0 |
| PROTEIN | 2.7272E−10 | 0 | 0 | 0 | 0 | 0 | 0 |
| KCL | 5.1453E−11 | 0 | 0 | 0 | 0 | 0 | 0 |
| $CASO_4$ | 5.1457E−11 | 0 | 0 | 0 | 0 | 0 | 0 |
| DAP | 3.8455E−11 | 0 | 0 | 0 | 0 | 0 | 0 |
| MAP | 2.2015E−10 | 0 | 0 | 0 | 0 | 0 | 0 |
| STARCH | 5.63471E−09 | 1.51588E−08 | 4.9456E−22 | 1.84498E−09 | 3.78971E−09 | 1.51588E−08 | 0 |
| Total Flow kg/hr | 61442.15 | 1561720 | 2042.168 | 40870.56 | 316050 | 1264200 | 297520 |
| Temperature C. | 29.3 | 27 | 31.5 | 31.5 | 31.5 | 31.5 | 35 |

TABLE 16B-continued

| Stream | 829 | 830 | 831 | 832 | 833 | 834 | 835 |
|---|---|---|---|---|---|---|---|
| Pressure psia | 0.61965831 | 14.696 | 0.61965831 | 0.61965831 | 29.392 | 29.392 | 14.696 |
| Suspended solids | | | | | | | |
| Mass Flow kg/hr | | | | | | | |
| PROTEIN | 0 | 0 | 0 | 0 | 0 | 0 | 0 |
| STARCH | 0 | 0 | 0 | 0 | 0 | 0 | 0 |
| FIBER | 0 | 0 | 0 | 0 | 0 | 0 | 0 |
| YEAST | 0 | 0 | 0 | 0 | 0 | 0 | 0 |
| Total Flow kg/hr | 0 | 0 | 0 | 0 | 0 | 0 | 0 |

While various embodiments of the present invention have been described above, it should be understood that they have been presented by way of example only, and not limitation. It will be apparent to persons skilled in the relevant art that various changes in form and detail can be made therein without departing from the scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for removing a product alcohol from a fermentation liquid, comprising:
   (a) at least partially vaporizing a fermentation liquid feed wherein a vapor stream is produced, the fermentation liquid feed and the vapor stream each comprising an amount of water, a product alcohol and $CO_2$; and
   (b) contacting the vapor stream with an absorption liquid under vacuum conditions wherein at least a portion of the vapor stream is absorbed into the absorption liquid to form an absorption liquid phase,
   wherein the portion of the vapor stream that is absorbed includes an amount of each of the water, the product alcohol, and the $CO_2$, and
   wherein the temperature at onset of the absorption of the vapor stream into the absorption liquid is greater than the temperature at onset of condensation of the vapor stream in the absence of the absorption liquid, and
   wherein heat of absorption generated by the contacting step (b) is used in the vaporizing step (a) at least partially vaporizing the fermentation liquid feed.

2. The method of claim 1, wherein the (a) vaporizing comprises:
   (i) removing the fermentation liquid feed from a fermentation vessel;
   (ii) supplying the fermentation liquid feed to a distillation column at a flow rate;
   (iii) distilling the fermentation liquid feed to produce the vapor stream enriched in the product alcohol and a bottoms stream depleted in the product alcohol, wherein the distilling occurs under a pressure sufficiently below atmospheric to allow for the vapor stream to be produced; and
   (iv) optionally, returning any portion of the bottoms stream to the fermentation vessel.

3. The method of claim 1, wherein step (b) further comprises optionally forming a residual vapor phase.

4. The method of claim 1, wherein the product alcohol is butanol.

5. The method of claim 4, wherein the product alcohol is isobutanol.

6. The method of claim 1, wherein the absorption liquid is ethylene glycol, ethylene glycol monomethyl ether, diethylene glycol, propylene glycol, dipropylene glycol, polyethylene glycols, polyethylene glycol ethers, polypropylene glycol ethers, or mixtures thereof.

7. The method of claim 1, wherein the absorption liquid is monoethanolamine, methylaminopropylamine, piperazine, diethanolamine, triethanolamine, diethylethanolamine, diisopropylamine, aminoethoxyethanol, dimethylaminopropanol, methyldiethanolamine, or mixtures thereof.

8. The method of claim 1, wherein the absorption liquid is 2-ethyl hexanol, isolauryl alcohol, isocetyl alcohol, oleyl alcohol, phenol, fatty acids, fatty esters, fatty alcohols, acids, alcohols, amides, amines, esters, ketones, carbonates, phosphates, salt solutions, or mixtures thereof.

9. The method of claim 1, wherein the absorption liquid is potassium carbonate in ethylene glycol solution.

10. The method of claim 1, further comprising distilling the absorption liquid phase containing the absorbed vapor stream under conditions sufficient to remove a substantial portion of the water, the product alcohol, and the $CO_2$ from the absorption liquid.

11. The method of claim 1, wherein a substantial portion of the $CO_2$ and at least a portion of at least one of the product alcohol and the water or both are absorbed into the absorption liquid.

12. The method of claim 11, wherein a substantial portion of each of the $CO_2$, the product alcohol, and the water are absorbed into the absorption liquid.

13. The method of claim 11, wherein a substantial portion of the product alcohol and at least a portion of the $CO_2$ and the water are absorbed into the absorption liquid.

14. The method of claim 11, wherein a substantial portion of the product alcohol and the $CO_2$ and at least a portion of the water are absorbed into the absorption liquid.

15. The method of claim 11, wherein a substantial portion of the product alcohol and the water and at least a portion of the $CO_2$ are absorbed into the absorption liquid.

16. The method of claim 1, further comprising, prior to the (a) vaporizing step, one or both of (i) gas stripping a portion of the $CO_2$ from the fermentation liquid feed and (ii) vaporizing a portion of the $CO_2$ from the fermentation liquid feed.

17. The method of claim 16, wherein a portion of the $CO_2$ from the fermentation liquid feed is gas stripped from the fermentation liquid feed prior to the (a) vaporizing step, where the portion of the $CO_2$ is gas stripped by countercurrent contact of the fermentation liquid feed with a noncondensible gas.

18. The method of claim 1, further comprising, prior to the (a) vaporizing step, gas stripping a substantial portion of the $CO_2$ and a portion of product alcohol from the fermentation liquid feed and vaporizing a portion of the $CO_2$ from the fermentation liquid feed.

* * * * *